United States Patent
Tamura et al.

(10) Patent No.: US 6,510,202 B2
(45) Date of Patent: Jan. 21, 2003

(54) IMAGING APPARATUS, IMAGING METHOD, AND STORAGE MEDIUM

(75) Inventors: Toshikazu Tamura, Tochigi (JP); Tatsuya Yamazaki, Tochigi (JP); Akira Hirai, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 14 days.

(21) Appl. No.: 09/821,517

(22) Filed: Mar. 29, 2001

(65) Prior Publication Data

US 2002/0001366 A1 Jan. 3, 2002

(30) Foreign Application Priority Data

Mar. 31, 2000 (JP) ........................................ 2000-096458
Mar. 31, 2000 (JP) ........................................ 2000-096463
Aug. 9, 2000 (JP) ........................................ 2000-241424

(51) Int. Cl.$^7$ ................................................. G21K 1/00
(52) U.S. Cl. ........................................ 378/155; 378/154
(58) Field of Search ................................ 378/154, 155, 378/98.8; 250/370.01, 370.08, 370.09

(56) References Cited

U.S. PATENT DOCUMENTS

| | | | | |
|---|---|---|---|---|
| 4,810,881 | A | 3/1989 | Berger et al. | 250/370.01 |
| 5,132,539 | A | 7/1992 | Kwasnick et al. | 250/361 |
| 5,379,335 | A | 1/1995 | Griesmer et al. | 378/155 |
| 5,381,014 | A | 1/1995 | Jeromin et al. | 250/370.09 |
| 5,396,072 | A | 3/1995 | Schiebel et al. | 250/370.09 |
| 5,418,377 | A | 5/1995 | Tran et al. | 250/483.1 |
| 6,304,632 | B1 * | 10/2001 | Rick et al. | 378/155 |

* cited by examiner

Primary Examiner—David P. Porta
(74) Attorney, Agent, or Firm—Morgan & Finnegan, LLP

(57) ABSTRACT

The object of this invention is to provide an imaging apparatus capable of providing a high-quality image optimum for medical diagnosis or the like by an arrangement for preventing any degradation in image quality due to the influence of electromagnetic noise and vibration caused by grid movement. In order to achieve this object, as operation control in receiving radiation transmitted through an object by an image sensing element through a movable grid and reading the accumulated signal from the image sensing element, a control device stops moving drive of the grid after the end of radiation irradiation for the object, and after the stop of moving drive, starts reading the accumulated signal from the image sensing element.

48 Claims, 19 Drawing Sheets

IMAGING APPARATUS, IMAGING METHOD, AND STORAGE MEDIUM

FIELD OF THE INVENTION

The present invention relates to an imaging apparatus, imaging method, and computer-readable storage medium which stores processing steps in executing the method, which are used for, e.g., an apparatus or system for performing radiation imaging of an object using a grid.

BACKGROUND OF THE INVENTION

Conventionally, a radiation method of irradiating an object with radiation such as X-rays and detecting the intensity distribution of the radiation transmitted through the object to acquire the radiation image of the object is widely used in the field of industrial non-destructive inspection or medical diagnosis.

In the most popular radiation imaging method, a combination of a so-called "screen" which emits fluorescent light by radiation and a silver halide film is used.

In the above radiation imaging method, first, an object is irradiated with radiation. The radiation transmitted through the object is converted into visible light by the screen to form a latent image on the silver halide film. After that, the silver halide film is chemically processed to acquire a visible image.

A thus obtained film image (radiation image) is a so-called analog picture and is used for medical diagnosis or inspection.

A computed radiography apparatus (to be referred to as a "CR apparatus" hereinafter) which acquires a radiation image using an imaging plate (to be referred to as an "IP" hereinafter) coated with a stimulable phosphor as a phosphor is also being put into practice.

When an IP primarily excited by radiation irradiation is secondarily excited by visible light such as a red laser beam, light called stimulable fluorescent light is emitted. The CR apparatus detects this light emission using a photosensor such as a photomultiplier to acquire a radiation image and outputs a visible image to a photosensitive material or CRT on the basis of the radiation image data.

Although the CR apparatus is a digital imaging apparatus, it is regarded as an indirect digital imaging apparatus because the image formation process, reading by secondary excitation, is necessary.

The reason for "indirect" is that the apparatus cannot instantaneously display the radiation image, like the above-described apparatus (to be referred to as an "analog imaging apparatus" hereinafter) which acquires an analog radiation image such as an analog picture.

In recent years, a technique has been developed, which acquires a digital radiation image using a photoelectric conversion device in which pixels formed from small photoelectric conversion elements or switching elements are arrayed in a matrix as an image detection means for acquiring a radiation image from radiation through an object.

Examples of a radiation imaging apparatus employing the above technique, i.e., having phosphors stacked on a sensor such as a CCD or amorphous silicon two-dimensional image sensing element are disclosed in U.S. Pat. Nos. 5,418,377, 5,396,072, 5,381,014, 5,132,539, and 4,810,881.

Such a radiation imaging apparatus can instantaneously display acquired radiation image data and is therefore regarded as a direct digital imaging apparatus.

As advantages of the indirect or direct digital imaging apparatus over the analog imaging apparatus, a filmless system, an increase in acquired information by image processing, and database construction become possible.

An advantage of the direct digital imaging apparatus over the indirect digital imaging apparatus is instantaneity. The direct digital imaging apparatus can be effectively used on, e.g., a medical scene with urgent need because a radiation image obtained by imaging can be immediately displayed at that place.

When the radiation imaging apparatus described above is used as a medical apparatus to detect the radiation transmission distribution of a patient as an object to be examined, a scattering ray removing member called a "grid" is normally inserted between the patient and a radiation transmission distribution detector (to be also simply referred to as a "detector" hereinafter) to reduce the influence of scattering rays generated when radiation is transmitted through the person to be examined.

A grid is formed by alternately arranging a thin foil of a material such as lead which hardly passes radiation and that of a material such as aluminum which readily passes radiation perpendicularly to the irradiation direction of radiation.

With this structure, radiation components such as scattering rays in the patient, which are generated when the patient is irradiated with radiation and have angles with respect to the axis of irradiation, are absorbed by the lead foil in the grid before they reach the detector. For this reason, a high-contrast image can be obtained.

If the grid stands still during imaging, the radiation reaching the lead in the grid is wholly absorbed including both the scattering rays and the primary rays of radiation. Since a distribution difference distribution corresponding to the array in the grid is formed at the detection section, a striped radiation image is detected, resulting in inconvenience in reading at the time of image diagnosis or the like.

A radiation imaging apparatus having a mechanism for moving the grid during imaging has already been placed on the market.

However, in the above-described conventional radiation imaging apparatus having a grid, a light receiving scheme using a sensor such as a CCD or amorphous silicon two-dimensional image sensing element is not used, and a signal read by a two-dimensional solid-state image sensing element is real-time electrical processing. For this reason, unlike an analog imaging apparatus or an indirect digital imaging apparatus such as a CR apparatus, the influence of vibration of the imaging section or the electromagnetic influence of the driving motor due to grid movement poses a problem.

More specifically, the vibration of the imaging section due to grid movement also vibrates the capacitor and signal lines. The weak electric capacitance varies, and noise is superposed on the radiation image.

Additionally, in the signal read by the sensor, when the motor is driven near the sensor to move the grid, the signal potential or control power supply potential varies due to the influence of electromagnetic noise, and noise is superposed on the radiation image.

The radiation image with noise superposed thereon may deteriorate, e.g., the medical diagnostic performance.

On the other hand, in the sensor such as a two-dimensional solid-state image sensing element, the amount of charges accumulated in the sensor increases in proportion to the signal accumulation time due to the influence of a dark current even in an unexposed state. The larger the amount of charges that do not contribute to an image signal becomes, the larger the noise added to the output image signal becomes.

Hence, imaging control is preferably optimized to make the accumulation time in the sensor as short as possible while eliminating the influence of grid vibration. Neither an apparatus nor system that implement such control are conventionally available.

In the conventional X-ray imaging apparatus, an X-ray beam is projected from an X-ray source through an object such as a medical patient to be analyzed. After the X-ray beam passes through the object to be examined, normally, an image intensifier converts the X-ray radiation into a visible light image, a video camera generates an analog video signal from the visible image, and the video signal is displayed on a monitor. Since an analog video signal is generated, image processing for automatic luminance adjustment and image enhancement is performed in an analog domain.

A solid-state X-ray detector having high resolving power has already been proposed, which is constructed by a two-dimensional array using 3,000 to 4,000 detection elements represented by photodiodes for each dimension. Each element generates an electrical signal corresponding to a pixel luminance of an X-ray image projected to the detector. The signals from the respective elements are individually read and digitized. Then, the signals are subjected to image processing, stored, and displayed.

A medical X-ray image need to have 4,096 or more grayscale levels. In addition, since the X-ray dose is preferably suppressed to reduce the exposure amount, the image signal amount is also limited. For this reason, an extremely noise-free system is required as compared to a general image sensing element.

In medical X-ray imaging, a grid is used to suppress the influence of X-ray scattering. A fixed grid is generally unsuitable to a solid-state X-ray image sensing element and poses a problem of aliasing, a system may be built using a movable grid.

As described above, a medical X-ray image sensing apparatus is required to be noise-free. A vibration caused by the movable grid can be a new noise source. The noise is generated by, e.g., the piezoelectric effect of a high-permittivity capacitor used in a circuit for generating a reference potential or simply because the parasitic capacitance in the read circuit varies due to the vibration.

To obtain the highest image quality, grid drive control, X-ray detector movement control, and X-ray detector driving method must be appropriately executed.

SUMMARY OF THE INVENTION

The present invention has been made to solve the above problem, and has as its object to provide an imaging apparatus, imaging method, and computer-readable storage medium which stores processing steps of executing the method, which can provide a high-quality image optimum for medical diagnosis or the like by an arrangement for preventing any degradation in image quality due to the influence of electromagnetic noise and vibration caused by grid movement.

It is another object of the present invention to provide an imaging apparatus and method which can easily and reliably obtain a satisfactory image without any influence of vibration of a grid or X-ray detection means by a very simple arrangement.

In order to achieve the above objects, an imaging apparatus according to the first aspect of the present invention is characterized by the following arrangement.

That is, there is provided an imaging apparatus which has a movable element related to imaging and an image sensing element, and has a function of sensing an image of an object with the image sensing element and reading as an image signal a signal generated by the image sensing element, comprising control means for stopping moving the element related to imaging, and after the stop of movement, starting reading the signal generated by the image sensing element.

An imaging apparatus according to the second aspect of the present invention is characterized by the following arrangement.

That is, there is provided an imaging apparatus which has a movable element related to imaging and an image sensing element, and has a function of sensing an image of an object with the image sensing element and reading as an image signal a signal generated by the image sensing element, comprising drive means for moving the element related to imaging by the image sensing element, and control means for controlling to cause the drive means to operate the element related to imaging at a predetermined speed without any acceleration during an operation period related to a read from the image sensing element.

An imaging apparatus according to the third aspect of the present invention is characterized by the following arrangement.

That is, there is provided an imaging apparatus which has a movable element related to imaging and an image sensing element, and has a function of sensing an image of an object with the image sensing element and reading as an image signal a signal generated by the image sensing element, comprising drive means for moving the element related to imaging by the image sensing element, and control means for controlling to cause the drive means to operate the element related to imaging at a uniform acceleration during an operation period related to a read from the image sensing element.

An imaging apparatus according to the fourth aspect of the present invention is characterized by the following arrangement.

That is, there is provided an imaging apparatus which has a movable element related to imaging and an image sensing element, and has a function of sensing an image of an object with the image sensing element and reading as an image signal a signal generated by the image sensing element, comprising drive means for moving the element related to imaging by the image sensing element, and control means for controlling to execute drive related to image acquisition upon determining that a value of a vibration is not more than a predetermined value during an operation period related to an image read from the image sensing element.

An imaging apparatus according to the fifth aspect of the present invention is characterized by the following arrangement.

That is, there is provided an imaging apparatus having a function of sensing an image of an object with an image sensing element and reading as an image signal a signal generated by the image sensing element, comprising drive means for moving the image sensing element, and control means for stopping moving the image sensing element by the drive means, and after the stop of movement, starting reading an accumulated signal from the image sensing element.

An imaging apparatus according to the sixth aspect of the present invention is characterized by the following arrangement.

That is, there is provided an imaging apparatus having a function of sensing an image of an object with an image sensing element and reading as an image signal a signal generated by the image sensing element, comprising drive means for moving the image sensing element, and control means for controlling to cause the drive means to operate the image sensing element at a predetermined speed without any acceleration during an operation period related to a read from the image sensing element.

An imaging apparatus according to the seventh aspect of the present invention is characterized by the following arrangement.

That is, there is provided an imaging apparatus having a function of sensing an image of an object with an image sensing element and reading as an image signal a signal generated by the image sensing element, comprising drive means for moving the image sensing element, and control means for controlling to cause the drive means to operate the image sensing element at a uniform acceleration during an operation period related to a read from the image sensing element.

An imaging apparatus according to the eighth aspect of the present invention is characterized by the following arrangement.

That is, there is provided an imaging apparatus having a function of sensing an image of an object with an image sensing element and reading as an image signal a signal generated by the image sensing element, comprising drive means for moving the image sensing element, and control means for controlling to execute drive related to image acquisition upon determining that a value of a vibration is not more than a predetermined value during an operation period related to an image read from the image sensing element.

An imaging method according to the first aspect of the present invention is characterized by the following step.

That is, there is provided an imaging method of sensing an image of an object with an image sensing element and reading a signal generated by the image sensing element while moving a movable element related to imaging, comprising the step of stopping moving the element related to imaging, and after the stop of movement, starting reading the signal from the image sensing element.

An imaging method according to the second aspect of the present invention is characterized by the following step.

That is, there is provided an imaging method of sensing an image of an object with an image sensing element and reading a signal generated by the image sensing element while moving a movable element related to imaging, comprising the step of, in moving the element related to imaging at the time of image sensing by the image sensing element, controlling to operate the element related to imaging at a predetermined speed without any acceleration during an operation period related to a read of the signal from the image sensing element.

An imaging method according to the third aspect of the present invention is characterized by the following step.

That is, there is provided an imaging method of sensing an image of an object with an image sensing element and reading a signal generated by the image sensing element while moving a movable element related to imaging, comprising the step of, in moving the element related to imaging at the time of image sensing by the image sensing element, controlling to operate the element related to imaging at a uniform acceleration during an operation period related to a read of the signal from the image sensing element.

An imaging method according to the fourth aspect of the present invention is characterized by the following step.

That is, there is provided an imaging method of sensing an image of an object with an image sensing element and reading a signal generated by the image sensing element while moving a movable element related to imaging, comprising the step of, in moving the element related to imaging at the time of image sensing by the image sensing element, controlling to execute drive related to image acquisition upon determining that a value of a vibration of the image sensing element is not more than a predetermined value during an operation period related to an image read from the image sensing element.

An imaging method according to the fifth aspect of the present invention is characterized by the following step.

That is, there is provided an imaging method of sensing an image of an object with a movable image sensing element and reading a signal generated by the image sensing element, comprising the step of stopping moving the image sensing element, and after the stop of movement, starting reading the signal from the image sensing element.

An imaging method according to the sixth aspect of the present invention is characterized by the following step.

That is, there is provided an imaging method of sensing an image of an object with a movable image sensing element and reading a signal generated by the image sensing element, comprising the step of controlling to operate the image sensing element at a predetermined speed without any acceleration during an operation period related to a read of the signal from the image sensing element.

An imaging method according to the seventh aspect of the present invention is characterized by the following step.

That is, there is provided an imaging method of sensing an image of an object with a movable image sensing element and reading a signal generated by the image sensing element, comprising the step of controlling to operate the image sensing element at a uniform acceleration during an operation period related to a read of the signal from the image sensing element.

An imaging method according to the eighth aspect of the present invention is characterized by the following step.

That is, there is provided an imaging method of sensing an image of an object with a movable image sensing element and reading a signal generated by the image sensing element, comprising the step of controlling to execute drive related to image acquisition upon determining that a value of a vibration of the image sensing element is not more than a predetermined value during an operation period related to an image read from the image sensing element.

A computer-readable storage medium according to the present invention is characterized in that the storage medium stores a processing program for executing the above imaging method.

Other objects and advantages besides those discussed above shall be apparent to those skilled in the art for the description of a preferred embodiment of the invention which follows. In the description, reference is made to accompanying drawings, which form a part hereof, and which illustrate an example of the invention. Such example, however, is not exhaustive of the various embodiments of the invention, and therefore reference is made to the claims which follow the description for determining the scope of the invention.

DETAILED DESCRIPTION OF THE PREFERRED EMBODIMENTS

Figure 1:
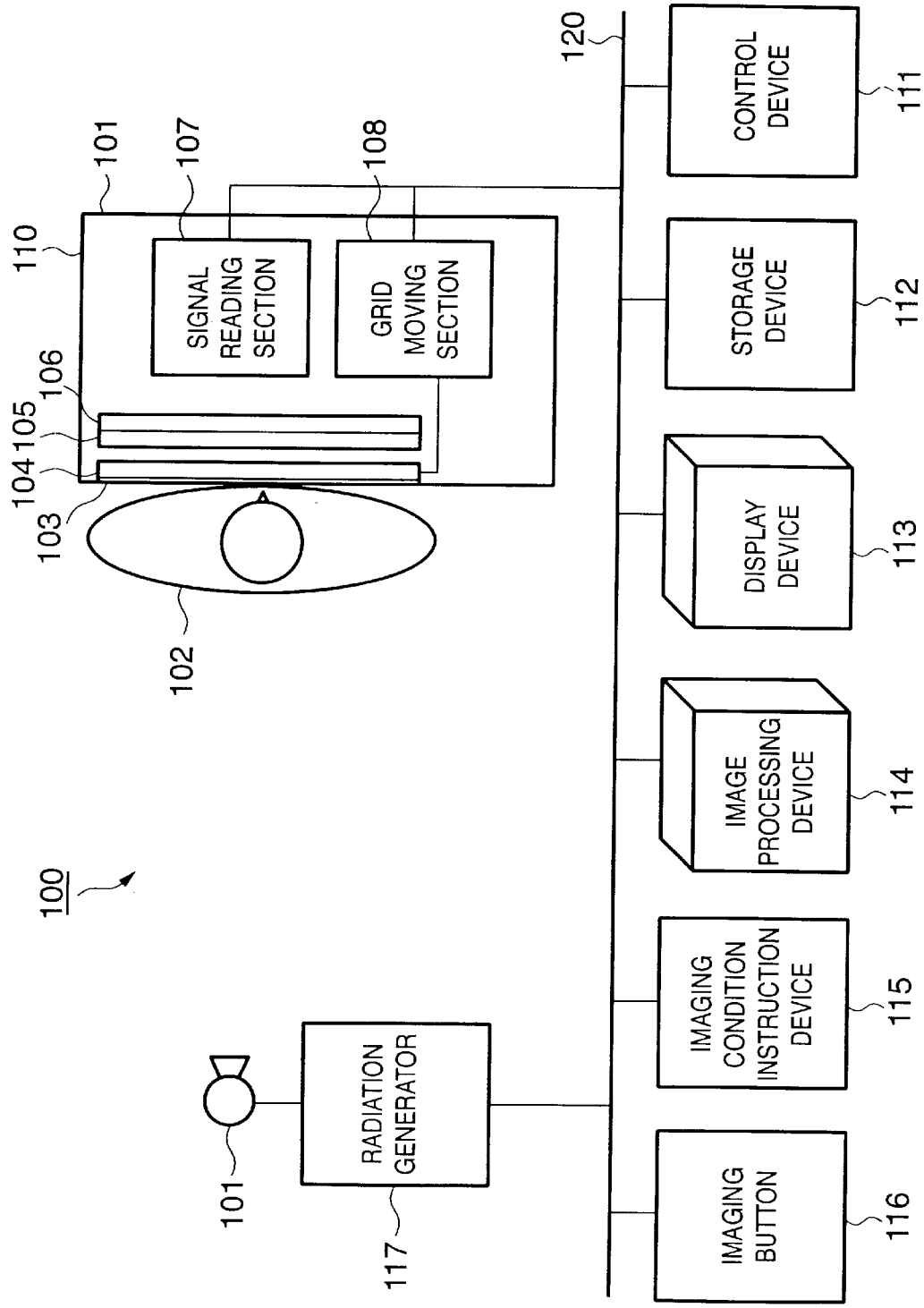
FIG. 1 is a block diagram showing the arrangement of a radiation imaging system according to the first embodiment, to which the present invention is applied.

The embodiments of the present invention will be described below with reference to the accompanying drawings.
(First Embodiment)
The present invention is applied to, e.g., a radiation imaging system 100 as shown in FIG. 1.
<Arrangement of Radiation Imaging System 100>
As shown in FIG. 1, the radiation imaging system 100 has an arrangement in which an imaging device 110 for acquiring an image signal of an object (patient) 102 to be examined, a control device 111 for controlling the entire system 100, a storage device 112 for storing various data such as a control program for control processing by the control device 111 and the image, a display device 113 for displaying the image or the like, an image processing device 114 for executing arbitrary image processing for the image signal of the patient 102, which is obtained by the imaging device 110, an imaging condition instruction device 115 for instructing various imaging conditions in the imaging device 110, an imaging button 116 for instructing the system 100 to start imaging operation, and a radiation generator 117 for generating a radiation (e.g., X-rays) from a radiation tube 101 to the patient 102 are connected to each other through a system bus 120 to exchange data.

The imaging device 110 is located at a position where the radiation generated from the radiation tube 101 of the radiation generator 117 can be received through the patient 102, and comprises a chest stand 103, grid 104, phosphor 105, sensor (two-dimensional solid-state image sensing element) 106, signal reading section 107, and grid moving section 108.

The chest stand 103, grid 104, phosphor 105, and sensor 106 are arranged in this order from the side of the radiation tube 101 of the radiation generator 117.
<Series of Operations of Radiation Imaging System 100>
Outlines of the imaging procedure and radiation image generation process in the radiation imaging system 100 will be described here.

The user (e.g., radiation technician) positions the patient 102 to the chest stand 103 and selectively inputs appropriate imaging conditions (e.g., tube voltage, tube current, irradiation time, type of sensor 106, and type of radiation tube 101) using the imaging condition instruction device 115.

In this embodiment, the imaging conditions are manually input by the user through the imaging condition instruction device 115. However, the present invention is not limited to this. For example, the imaging conditions may be input through a network (not shown) connected to the imaging device 110.

Next, the user presses the imaging button 116 to request the control device 111 to start imaging operation.

After receiving the imaging operation start request from the user, the control device 111 performs initialization necessary in the system 100 and prompts the radiation generator 117 to irradiate the person with radiation.

In accordance with the irradiation instruction from the control device 111, the radiation generator 117 generates radiation from the radiation tube 101.

The radiation generated from the radiation tube 101 passes through the patient 102 and reaches chest stand 103.

The chest stand 103 is exposed by the radiation transmitted through the patient 102 with a transmitted radiation distribution in accordance with the structure in the patient 102.

Since the chest stand 103 is sufficiently transparent to the radiation, the radiation transmitted through the chest stand 103 reaches the grid 104.

The grid 104 removes scattering ray components in the radiation transmitted through the chest stand 103 and sends only effective radiation components to the phosphor 105.

The phosphor 105 converts the radiation (effective radiation) from the grid 104 into visible light in accordance with the spectral sensitivity of the sensor 106.

The sensor 106 receives the radiation from the phosphor 105, converts the radiation light into an electrical signal (image signal) by two-dimensional photoelectric conversion, and accumulates it.

The present invention is not limited to this. The sensor 106 may directly convert the radiation from the grid 104 to the electrical signal (image signal).

The signal reading section 107 reads the image signal accumulated in the sensor 106 and stores the signal in the storage device 112 as a radiation image signal.

The image processing device 114 performs appropriate image processing for the radiation image signal stored in the storage device 112.

Figure 2:
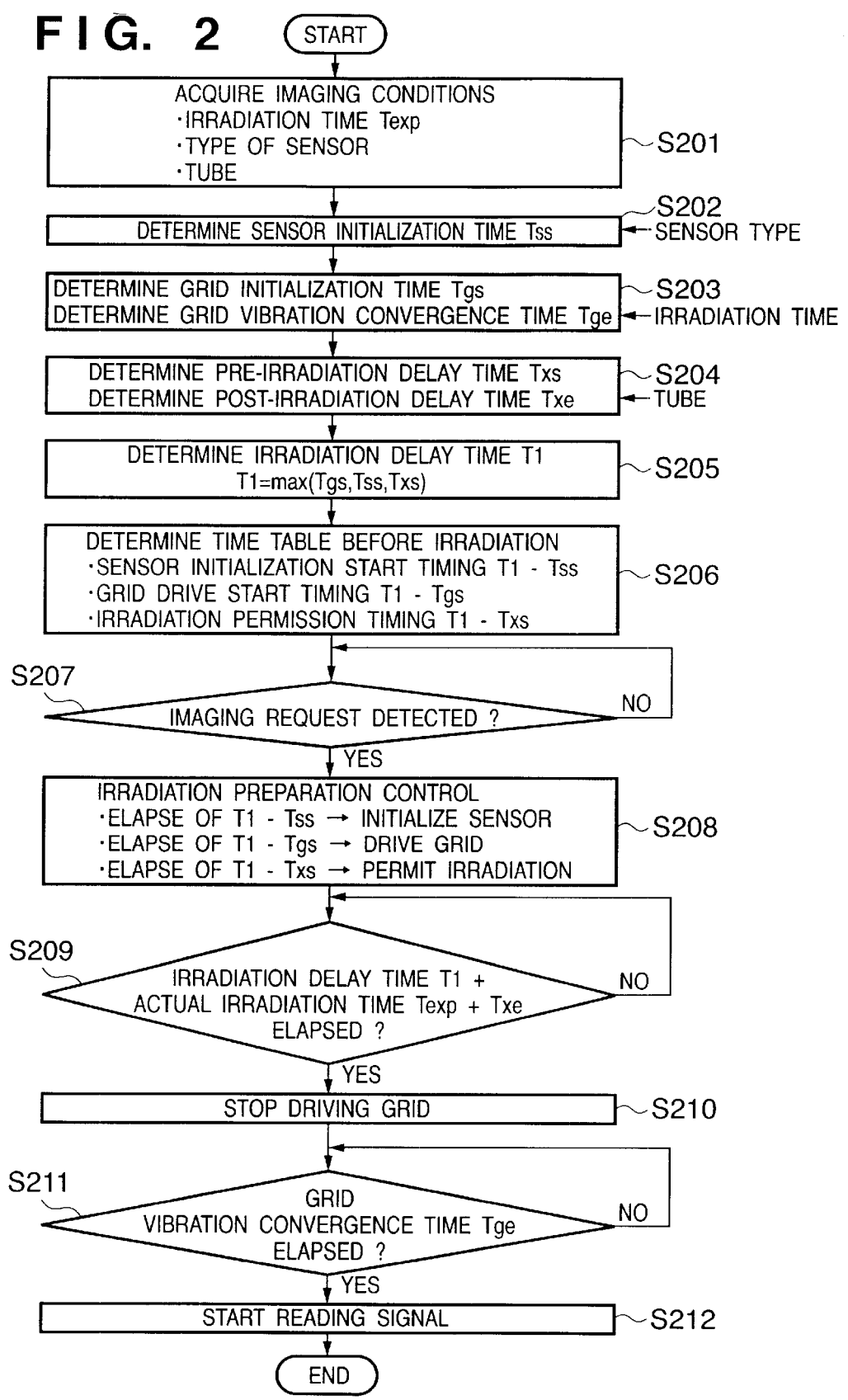
FIG. 2 is a flow chart for explaining operation of the radiation imaging system.

The display device 113 displays the radiation image signal after processing by the image processing device 114.
<Most Characteristic Operation and Arrangement of Radiation Imaging System 100>
FIG. 2 is a flow chart showing operation control processing executed by the control device 111 for the system 100.

FIGS. 3A to 3F are timing charts showing the operation control timing.

The processing shown in FIG. 2 corresponds to processing from the above-described imaging condition input by the user to image signal read from the sensor 106.

Step S201

The control device 111 recognizes an irradiation time T exp, the type of sensor 106 used for imaging, and the type of radiation tube 101 on the basis of imaging conditions selectively input by the user through the imaging condition instruction device 115.

In accordance with the recognized information, the control device 111 determines control until radiation irradiation and control after radiation irradiation by processing from step S202.

Step S202

The control device 111 determines a sensor initialization time Tss in accordance with the type of sensor 106.

The sensor initialization time Tss changes depending on the type of sensor 106. For example, when the sensor 106 requires predischarge of a dark current, the pre-read time is the sensor initialization time Tss. From this time, signal accumulation in the sensor 106 starts.

Step S203

The control device 111 determines a grid initialization time Tgs and grid vibration convergence time Tge from the irradiation time T exp.

More specifically, to reduce stripe image formation on the object by the grid 104, for example, radiation must be transmitted through stripes of 10 or more cycles. However, the moving distance of the grid 104 is limited. Hence, the moving speed of the grid 104 must be optimized in accordance with the irradiation time T exp. In addition, since the grid 104 generally has a focal point, the irradiation central position of radiation and the central position of the grid 104 must be aligned to obtain an image with a satisfactory quality.

Hence, a time required until the optimum moving speed (target moving speed) of the grid 104 is obtained and the position of the grid 104 reaches the irradiation central position (target position) of radiation corresponds to the grid initialization time Tgs.

In this embodiment, the grid initialization times Tgs until the target moving speed and position of the grid 104 are obtained and the grid vibration convergence times Tge required to converge device vibration caused by movement are obtained as a table by experiments in correspondence with, e.g., various patterns of irradiation time T exp and moving speed of the grid 104 and stored in the storage device 112 in advance. The grid initialization time Tgs and grid vibration convergence time Tge corresponding to the actually obtained irradiation time T exp are determined from the table information in the storage device 112.

Step S204

The control device 111 determines a pre-irradiation delay time Txs and post-irradiation delay time Txe on the basis of the type of radiation tube 101.

The pre-irradiation delay time Txs is a time after the radiation generator 117 is instructed to permit radiation irradiation until the radiation generator 117 actually starts radiation irradiation, and is determined by the type of radiation generator 117 or radiation tube 101.

In this embodiment, the pre-irradiation delay times Txs corresponding to, e.g., various types of radiation generator 117 or radiation tube 101 are prepared as a table in advance, and a corresponding pre-irradiation delay time Txs is determined from the table information.

The post-irradiation delay time Txe is a delay time after the elapse of irradiation time T exp until the radiation generator 117 actually ends the radiation irradiation. The post-irradiation delay time Txe is also determined in accordance with the same procedure as that for the pre-irradiation delay time Txs.

Step S205

The control device 111 determines an irradiation delay time T1.

The irradiation delay time T1 is a delay time after an imaging request is input by the user through the imaging button 116 until the radiation generator 117 actually starts radiation irradiation. Of the sensor initialization time Tss determined in step S202, the grid initialization time Tgs determined in step S203, and the pre-irradiation delay time Txs determined in step S204, the longest time is determined as the irradiation delay time T1.

Step S206

The control device 111 determines a time table before irradiation.

This time table is determined from the sensor initialization time Tss determined in step S202, the grid initialization time Tgs determined in step S203, and the pre-irradiation delay time Txs determined in step S204.

More specifically, the control sequence and times (timings) of initialization of the sensor 106, start of drive of the grid 104, and radiation irradiation instruction (irradiation permission) to the radiation generator 117 after the imaging request input by the user through the imaging button 116 is recognized are determined by subtracting each delay time from the irradiation delay time T1 determined in step S205.

The initialization timing of the sensor 106 is determined as "T1−Tss". The drive start timing of the grid 104 is determined as "T1−Tgs". The radiation irradiation instruction (irradiation permission) timing for the radiation generator 117 is determined as "T1−Txs".

Step S207

After control before radiation irradiation is determined in the above-described way, the control device 111 determines whether an imaging request is input by the user through the imaging button 116 and stands by until an imaging request is received.

Step S208

Upon recognizing that an imaging request is input by the user through the imaging button 116, the control device 111 executes operation control according to the time table determined in step S206.

Initialization of the sensor 106 is started after the elapse of "T1−Tss", drive of the grid 104 is started after the elapse of "T1−Tgs", and irradiation permission is executed after the elapse of "T1−Txs".

Step S209

The control device 111 stands by until the total time (T1+T exp+Txe) of the irradiation time (actual exposure time) T exp determined in step S201, the post-irradiation delay time Txe determined in step S204, and the irradiation delay time T1 determined in step S205 elapses.

Step S210

When recognizing that the time (T1+T exp+Txe) has elapsed, the control device 111 stops driving the grid 104 through the grid moving section 108.

Step S211

The control device 111 stands by until the grid vibration convergence time Tge determined in step S203 elapses.

Step S212

When recognizing that the grid vibration convergence time Tge has elapsed, the control device 111 causes the signal reading section 107 to start reading the signal accumulated in the sensor 106.

In the operation control for the radiation imaging system 100 shown in the flow chart of FIG. 2, especially, since the operation stands by for the post-irradiation delay time Txe after the elapse of irradiation time T exp, stripe image formation on the object by the grid 104 can be prevented.

In addition, since drive of the grid 104 is stopped, the influence of electromagnetic noise generated from the grid moving section 108 can be prevented.

Furthermore, since the operation stands by for the grid vibration convergence time Tge after the stop of drive of the grid 104, the influence of device vibration can be prevented.

Hence, after the imaging request from the user is recognized, the control device 111 controls the operation of the system 100 in accordance with the flow chart in FIG. 2, thereby acquiring a satisfactory image.

The above operation control for the radiation imaging system 100 will be described below in more detail with reference to the timing charts shown in FIGS. 3A to 3F.

The timing charts of FIGS. 3A to 3F explain timings after the imaging button 116 is pressed.

In accordance with the imaging conditions input by the user, for example,

Irradiation time T exp=100 ms

Sensor initialization time Tss=200 ms

Grid initialization time Tgs=300 ms

Pre-irradiation delay time Txs=100 ms

Grid vibration convergence time Tge=300 ms

Post-irradiation delay time Txe=100 ms are determined.

In this case, the irradiation delay time T1 as the longest time of the sensor initialization time Tss, grid initialization time Tgs, and pre-irradiation delay time Txs is determined by $$T1 = \max(Tss, Tgs, Txs) = Tgs = 300 \text{ ms}$$

Operation control until radiation irradiation is determined from these initial conditions.

Next, control timings for sensor initialization, start of grid movement, and irradiation permission instruction after recognition of the imaging request are determined by subtracting a corresponding time required for operation from the irradiation delay time T1.

Sensor initialization timing: $T1-Tss=100$ ms

Grid movement start timing: $T1-Tgs=0$ ms

Irradiation enable signal transmission timing: $T1-Txs=200$ ms

Control timings after radiation irradiation are so determined that movement control for the grid 104 is stopped after the elapse of actual irradiation time obtained by adding the irradiation time T exp and post-irradiation delay time Txe to the irradiation delay T1, and the signal read from the sensor 106 is started after the elapse of grid vibration convergence time Tge.

That is, the grid control stop timing and signal read start timing are determined by Grid control stop timing: $T1+T \text{ exp}+Txe=500$ ms Signal read start timing: $T1+T \text{ exp}+Txe+Tge=800$ ms After the control timings are determined, an imaging request (FIG. 3A) input by the user by pressing the imaging button 116 is waited.

When an imaging request is recognized, operation control for the radiation imaging system 100 is started on the basis of the determined control timings.

Figure 3:
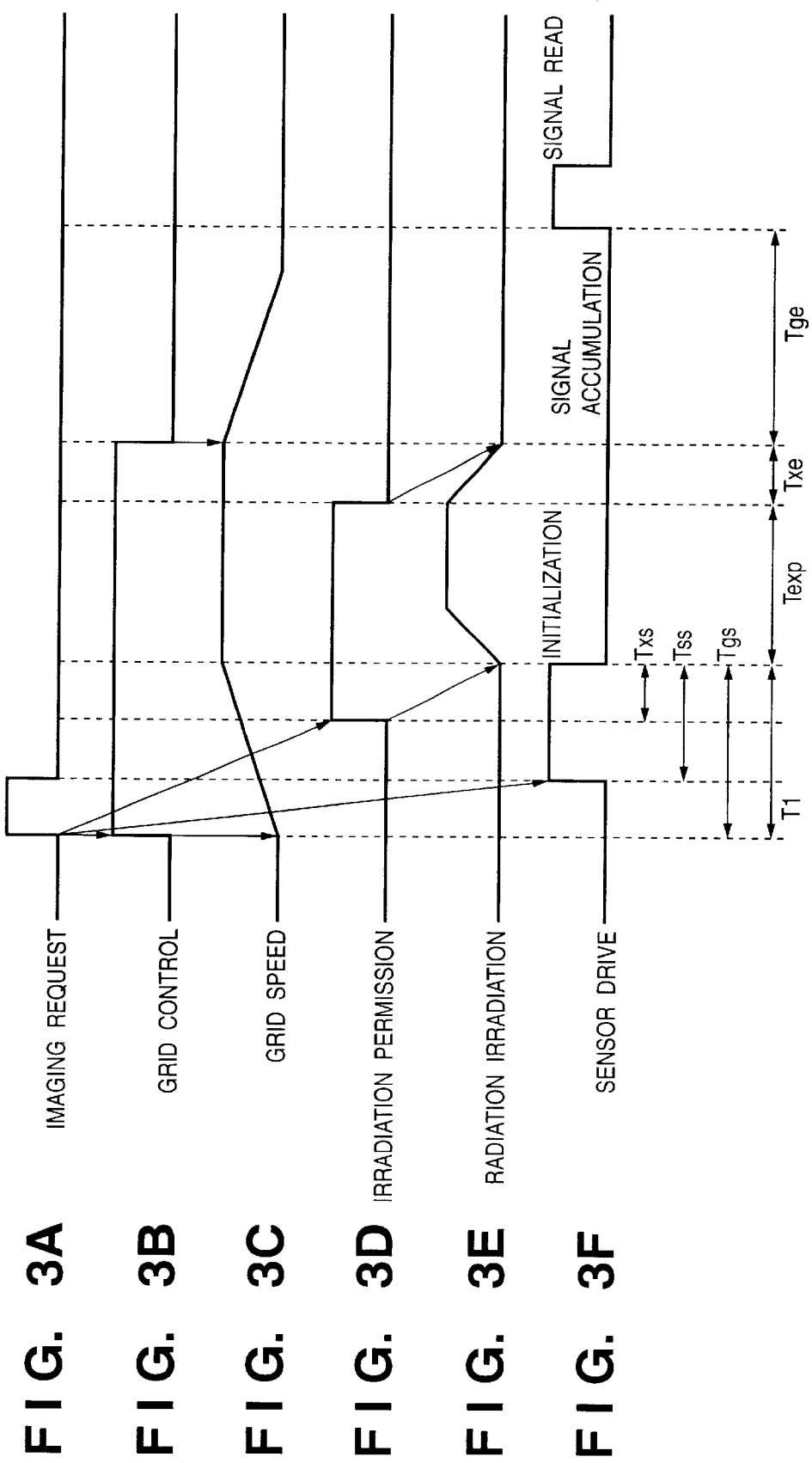
FIGS. 3A to 3F are timing charts for explaining the operation control timing of the radiation imaging system.

First, movement (motion) of the grid 104 is started, as shown in FIG. 3B.

The moving speed of the grid 104 acceleratingly increases and reaches an irradiation enable state after the elapse of 300 ms (grid initialization time Tgs=300 ms), as shown in FIG. 3C.

Next, as shown in FIG. 3F, after the elapse of 100 ms (sensor initialization timing: T1−Tss=100 ms) from imaging request recognition, initialization of the sensor 106 is started. After the elapse of 200 ms (sensor initialization time Tss=200 ms), initialization of the sensor 106 is ended.

As shown in FIG. 3D, after the elapse of 200 ms (irradiation enable signal transmission timing: T1−Txs=200 ms) from imaging request recognition, the radiation generator 117 is instructed to start irradiation.

The radiation generator 117 starts actual irradiation after the elapse of 100 ms (pre-irradiation delay time Txs=100 ms), as shown in FIG. 3E.

After the elapse of 500 ms (grid control stop timing: T1+T exp+Txe=500 ms) from imaging request recognition, actual irradiation by the radiation generator 117 is ended.

At this time, movement control for the grid 104 is stopped, as shown in FIG. 3B, and the moving speed of the grid 104 gradually decreases. Along with this deceleration, the vibration of the imaging device 110, that is generated by moving the grid 104, starts converging.

After that, as shown in FIG. 3F, after the elapse of 800 ms (signal read start timing: T1+T exp+Txe+Tge=800 ms) from imaging request recognition, the signal reading section 107 is instructed to end signal accumulation in the sensor 106 and start reading the signal.

At this time, the vibration of the imaging device 110 has become so small that it does not affect the image quality. As a result, a satisfactory image can be obtained.

(Second Embodiment)

Figure 4:
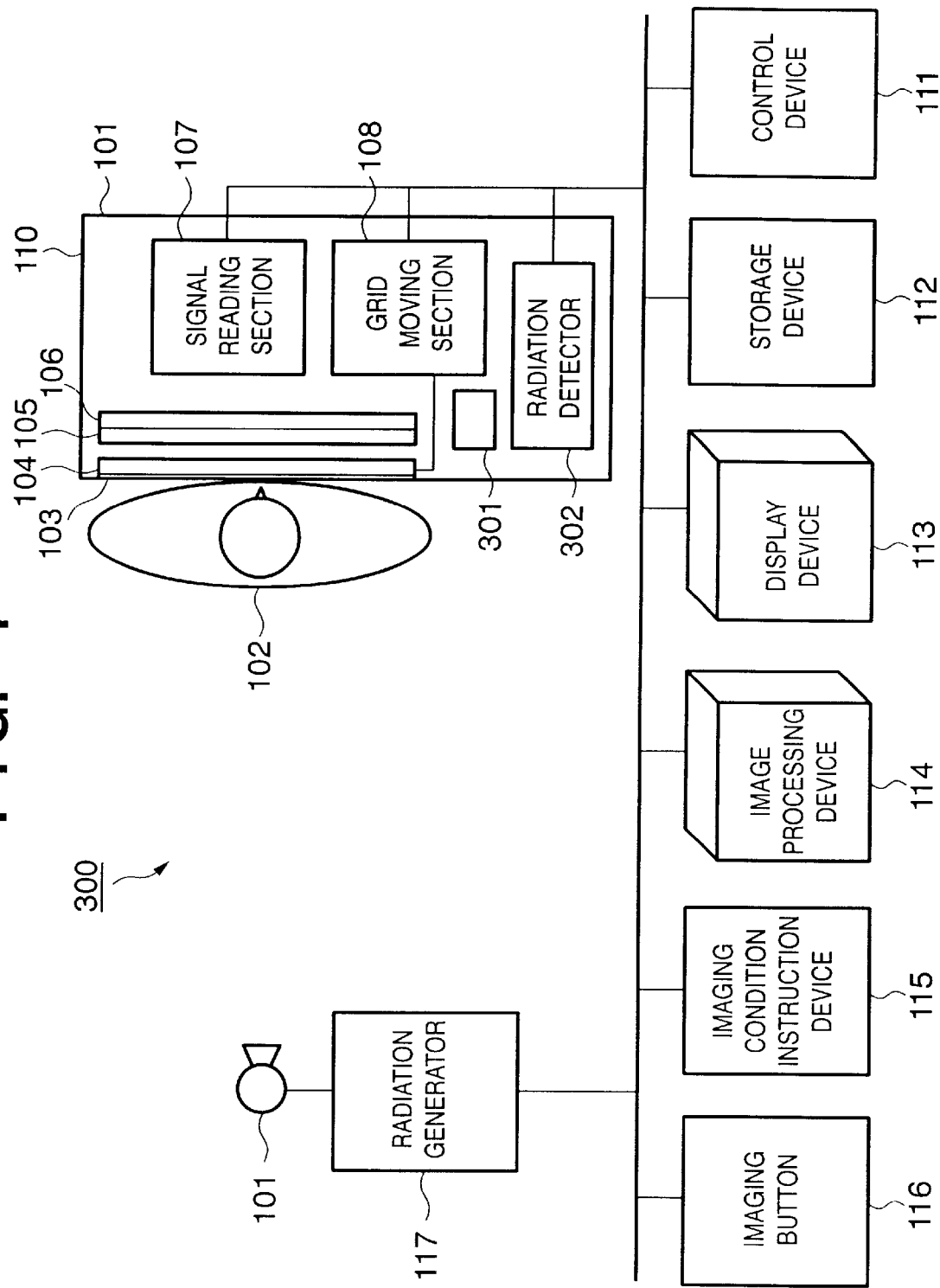
FIG. 4 is a block diagram showing the arrangement of a radiation imaging system according to the second embodiment, to which the present invention is applied.

The present invention is applied to, e.g., a radiation imaging system 300 as shown in FIG. 4.

This radiation imaging system 300 has the same arrangement as that of the radiation imaging system 100 shown in FIG. 1 except that a radiation detector 302 for detecting a radiation irradiation state and an vibration measurement device 301 for measuring the vibration state of a grid 104 are prepared in an imaging device 110.

The same reference numerals as in the radiation imaging system 100 shown in FIG. 1 denote the same parts in the radiation imaging system 300 shown in FIG. 4, and a detailed description thereof will be omitted. Only parts different from the radiation imaging system 100 in FIG. 1 will be described in detail.

Figure 5:
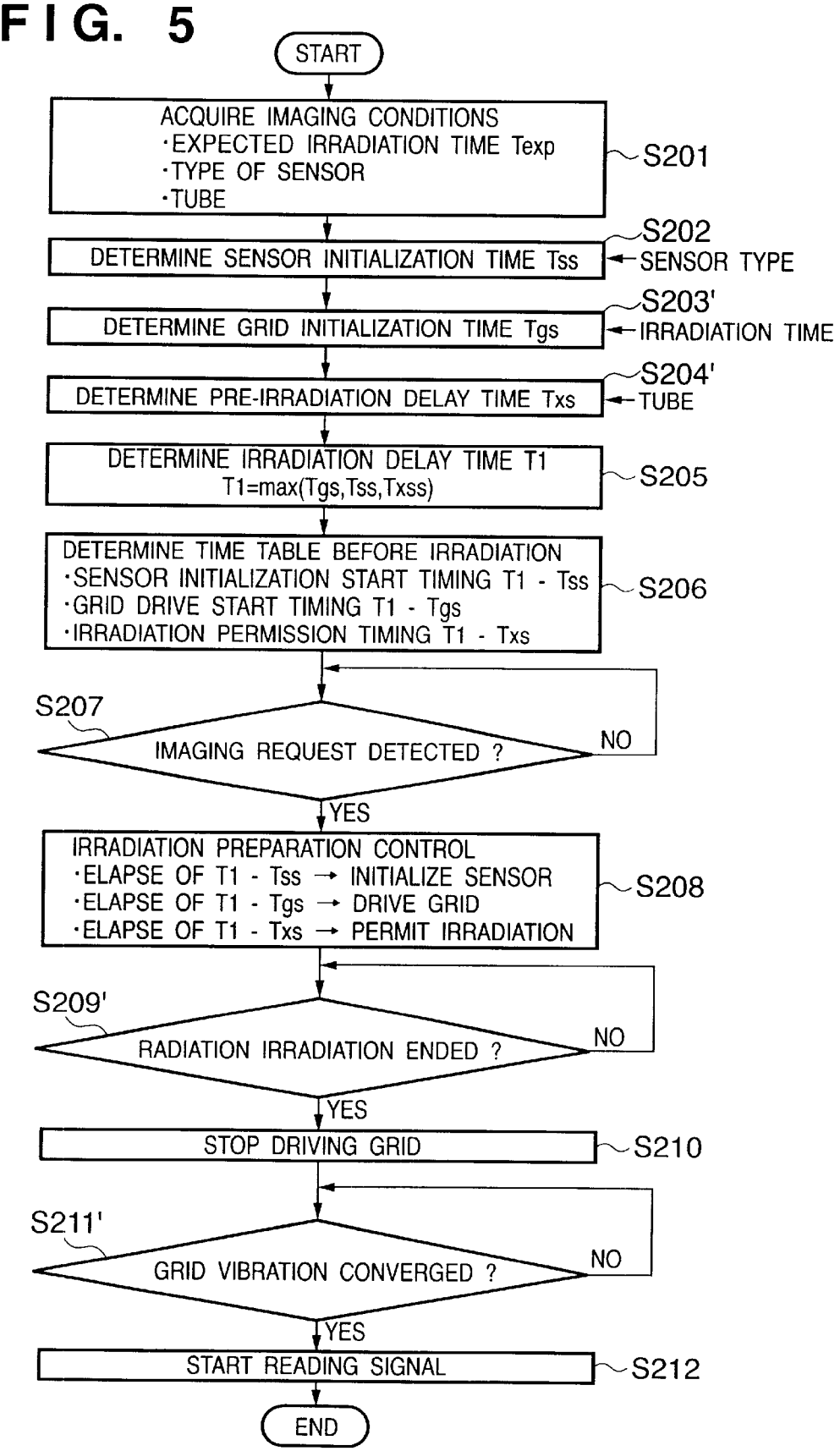
FIG. 5 is a flow chart for explaining operation of the radiation imaging system.

FIG. 5 is a flow chart showing operation control processing executed by a control device 111 of this embodiment for the system 300. FIGS. 6A to 6H are timing charts showing the operation control timing.

The same step numbers as in the flow chart of FIG. 2 denote the same processing steps in the flow chart of FIG. 5, and a detailed description thereof will be omitted.

Step S201

The control device 111 recognizes an irradiation time T exp, the type of sensor 106 used for imaging, and the type of radiation tube 101 on the basis of imaging conditions selectively input by the user through an imaging condition instruction device 115.

In accordance with the recognized information, the control device 111 determines control until radiation irradiation and control after radiation irradiation by processing from step S202.

Step S202

The control device 111 determines a sensor initialization time Tss in accordance with the type of sensor 106.

Step S203'

The control device 111 determines a grid initialization time Tgs (time until the grid 104 reaches the target moving speed and position) from the irradiation time T exp.

Step S204'

The control device 111 determines a pre-irradiation delay time Txs (time after radiation irradiation permission is instructed to a radiation generator 117 until the radiation generator 117 actually starts radiation irradiation) on the basis of the type of radiation tube 101.

Step S205

The control device 111 determines an irradiation delay time T1 (the longest time of the sensor initialization time Tss, grid initialization time Tgs, and pre-irradiation delay time Txs).

Step S206

The control device 111 determines, as a time table before irradiation, the initialization timing of the sensor 106 as "T1–Tss", the drive start timing of the grid 104 as "T1–Tgs", and the radiation irradiation instruction (irradiation permission) timing for the radiation generator 117 as "T1–Txs".

Step S207

After control before radiation irradiation is determined in the above-described way, the control device 111 determines whether an imaging request is input by the user through an imaging button 116 and stands by until an imaging request is received.

Step S208

Upon recognizing that an imaging request is input by the user through the imaging button 116, the control device 111 executes operation control according to the time table determined in step S206.

Initialization of the sensor 106 is started after the elapse of "T1–Tss", drive of the grid 104 is started after the elapse of "T1–Tgs", and irradiation permission is executed after the elapse of "T1–Txs".

Step S209'

The control device 111 determines on the basis of a detection signal output from the radiation detector 302 whether radiation irradiation by the radiation generator 117 is ended.

Step S210

Upon recognizing that radiation irradiation by the radiation generator 117 is ended, the control device 111 stops driving the grid 104 through a grid moving section 108.

Step S211'

The control device 111 determines on the basis of a measurement result from the vibration measurement device 301 whether the vibration of the grid 104 has converged.

Step S212

When recognizing that the vibration of the grid 104 has converged, the control device 111 causes a signal reading section 107 to start reading the signal accumulated in the sensor 106.

In the operation control for the radiation imaging system 300 shown in the flow chart of FIG. 5, especially when the end of radiation irradiation is recognized in accordance with the detection result from the radiation detector 302, drive of the grid 104 is stopped. For this reason, the influence of electromagnetic noise generated from the grid moving section 108 can be prevented.

Furthermore, since the operation stands until it is determined on the basis of the measurement result from the vibration measurement device 301 that the vibration of the grid 104 has converged after the stop of drive of the grid 104, the influence of device vibration can be prevented.

Hence, after the imaging request from the user is recognized, the control device 111 controls the operation of the system 300 in accordance with the flow chart in FIG. 5, thereby acquiring a satisfactory image.

The above operation control for the radiation imaging system 300 will be described below in more detail with reference to the timing charts shown in FIGS. 6A to 6H.

The timing charts of FIGS. 6A to 6H explain timings after the imaging button 116 is pressed.

In accordance with the imaging conditions input by the user, for example,

Irradiation time T exp=100 ms

Sensor initialization time Tss=200 ms

Grid initialization time Tgs=300 ms

Pre-irradiation delay time Txs=100 ms are determined.

In this case, the irradiation delay time T1 as the longest time of the sensor initialization time Tss, grid initialization time Tgs, and pre-irradiation delay time Txs is determined by $$T1=\max(Tss, Tgs, Txs)=Tgs=300 \text{ ms}$$

Operation control until radiation irradiation is determined from these initial conditions.

Next, control timings for sensor initialization, start of grid movement, and irradiation permission instruction after recognition of the imaging request are determined by subtracting a corresponding time required for operation from the irradiation delay time T1.

Sensor initialization timing: $T1-Tss=100$ ms

Grid movement start timing: $T1-Tgs=0$ ms

Irradiation enable signal transmission timing: $T1-Txs=200$ ms

After the control timings are determined, an imaging request (FIG. 6A) input by the user by pressing the imaging button 116 is waited.

When an imaging request is recognized, operation control for the radiation imaging system 300 is started on the basis of the determined control timings.

Figure 6:
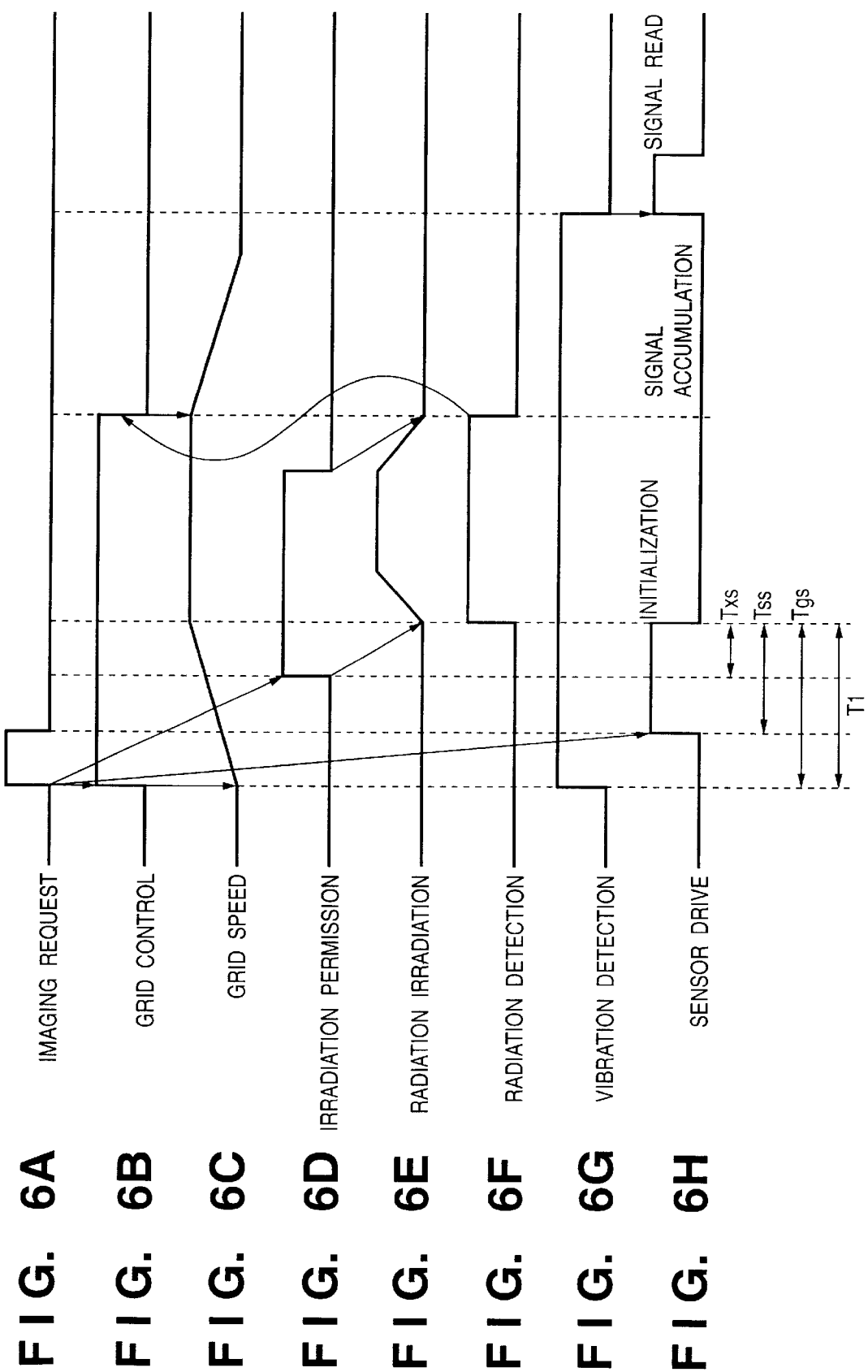
FIGS. 6A to 6H are timing charts for explaining the operation control timing of the radiation imaging system.

First, movement (motion) of the grid 104 is started, as shown in FIG. 6B. Simultaneously, the vibration detection signal representing that the grid 104 is in a moving state is set at High level, as shown in FIG. 6G.

The moving speed of the grid 104 acceleratingly increases and reaches an irradiation enable state after the elapse of 300 ms (grid initialization time Tgs=300 ms), as shown in FIG. 6C.

Next, as shown in FIG. 6H, after the elapse of 100 ms (sensor initialization timing: T1–Tss=100 ms) from imaging request recognition, initialization of the sensor 106 is started. After the elapse of 200 ms (sensor initialization time Tss=200 ms), initialization of the sensor 106 is ended.

As shown in FIG. 6D, after the elapse of 200 ms (irradiation enable signal transmission timing: T1–Txs=200 ms) from imaging request recognition, the radiation generator 117 is instructed to start irradiation.

The radiation generator 117 starts actual irradiation after the elapse of 100 ms (pre-irradiation delay time Txs=100 ms), as shown in FIG. 6E. Simultaneously, the radiation detection signal representing radiation irradiation is set at High level, as shown in FIG. 6F.

When radiation irradiation is ended, and the output from the radiation detector 302 becomes smaller than a predetermined threshold value, it is determined that irradiation is ended. As shown in FIG. 6F, the radiation detection signal is set at Low level. Along with this processing, movement control for the grid 104 is stopped, as shown in FIG. 6B. The moving speed of the grid 104 gradually decreases. The vibration state of the grid 104 at this time is observed by the vibration measurement device 301.

When the vibration of the imaging device 110, that is generated by moving the grid 104, starts converging, and it is recognized that the output from the vibration measurement device 301 becomes smaller than a predetermined vibration amount, the vibration detection signal is set at Low level, as shown in FIG. 6G.

As shown in FIG. 6F, the signal reading section 107 is instructed to end signal accumulation in the sensor 106 and start reading the signal.

At this time, the vibration of the imaging device 110 has become so small that it does not affect the image quality. As a result, a satisfactory image can be obtained.

The object of the present invention is achieved even by supplying a storage medium which stores software program codes for implementing the functions of the host and terminal the first and second embodiments to a system or apparatus and causing the computer (or a CPU or MPU) of the system or apparatus to read and execute the program codes stored in the storage medium.

In this case, the program codes read from the storage medium implement the functions of the first and second embodiments by themselves, and the storage medium which stores the program codes constitutes the present invention.

As a storage medium for supplying the program codes, for example, a ROM, a floppy disk, hard disk, optical disk, magnetooptical disk, CD-ROM, CD-R, magnetic tape, nonvolatile memory card or the like can be used.

The functions of the first and second embodiments are implemented not only when the readout program codes are executed by the computer but also when the operating system (OS) running on the computer performs part or all of actual processing on the basis of the instructions of the program codes.

The functions of the first and second embodiments are also implemented when the program codes read from the storage medium are written in the memory of a function expansion board inserted into the computer or a function expansion unit connected to the computer, and the CPU of the function expansion board or function expansion unit performs part or all of actual processing on the basis of the instructions of the program codes.

As described above, according to the above embodiments, since the grid is stopped before the read of the signal accumulated in the image sensing element is started, the influence of electromagnetic noise due to grid movement can be eliminated. Hence, no noise is superposed on the image (radiation image or the like) obtained from the read signal from the image sensing element, and high-quality image can be obtained.

When a predetermined standby time is set from the stop of the grid, the signal read from the image sensing element starts after the influence of vibration of the imaging element due to grid movement is reduced. For this reason, an image with a higher quality can be obtained.

Hence, the quality of the image can be prevented from degrading due to the influence of electromagnetic noise upon grid movement. In addition, the quality of the image can be prevented from degrading due to the influence of vibration of the image sensing element upon grid movement.

For example, when the above embodiments are applied to radiation imaging, a satisfactory radiation image free from noise can be provided. For this reason, a diagnostic error in image diagnosis can be reliably prevented.

(Third Embodiment)

Figure 7:
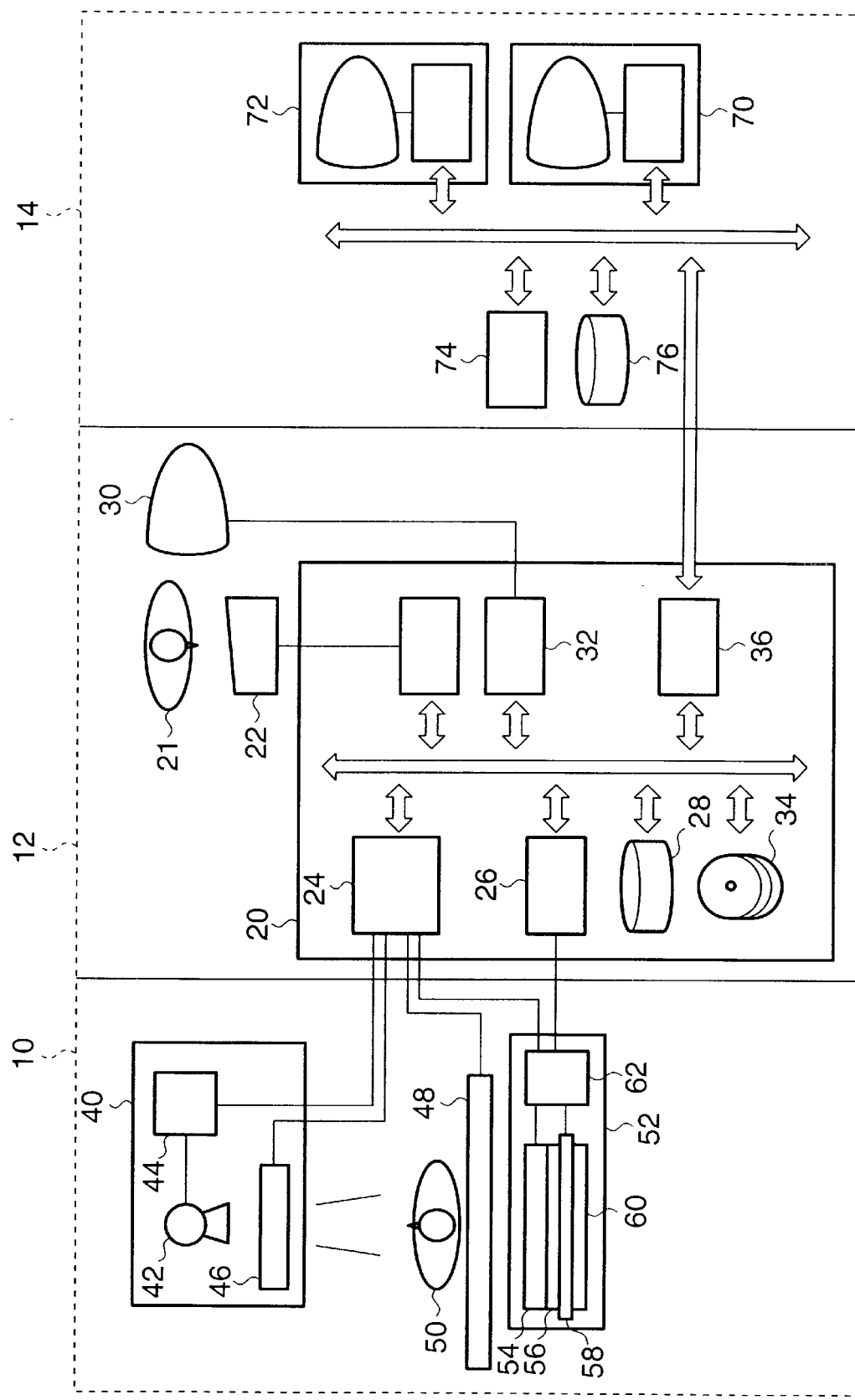
FIG. 7 is a view showing the schematic arrangement of an X-ray image sensing system.

FIG. 7 is a block diagram showing the arrangement of an X-ray image sensing system according to the third embodiment of the present invention.

Reference numeral 10 denotes an X-ray room; 12, an X-ray control room; and 14, a diagnosis room.

The X-ray control room 12 has a system controller 20 for controlling the entire operation of the X-ray image sensing system. An operator interface 22 having an X-ray exposure request switch, touch panel, mouse, keyboard, joystick, foot switch, and the like is used by an operator 21 to input various instructions to the system controller 20. The contents of instructions by the operator 21 are, e.g., imaging conditions (still/moving image, X-ray tube voltage, tube current, and X-ray irradiation time), imaging timing, image processing conditions, ID of a patient, and processing method for a read image. An image sensing controller 24 controls the X-ray image sensing system placed in the X-ray room 10. An image processor 26 processes an image obtained by the X-ray image sensing system in the X-ray room 10. Image processing by the image processor 26 includes, e.g., image data correction, space filtering, recursive processing, grayscale processing, scattered ray correction, and dynamic range (DR) compression processing.

A large-capacity high-speed storage device 28 stores basic image data processed by the image processor 26 and is formed from, e.g., a hard disk array such as a RAID. A monitor display (to be referred to as a monitor hereinafter) 30 displays an image. A display controller 32 controls the monitor 30 to make it display various characters and images. Reference numeral 34 denotes a large-capacity external storage device (e.g., a magnetooptical disk). A LAN board 36 connects the X-ray control room 12 to the diagnosis room 14 to transfer, e.g., an image obtained in the X-ray room 10 to the apparatus in the diagnosis room 14.

An X-ray generator 40 for generating X-rays is placed in the X-ray room 10. The X-ray generator 40 comprises an X-ray tube 42 for generating X-rays, a high-voltage source 44 controlled by the image sensing controller 24 to drive the X-ray tube 42, and an X-ray stop 46 for converging an X-ray beam generated by the X-ray tube 42 to a desired image sensing region. A patient 50 as an object to be examined lies on an imaging bed 48. The imaging bed 48 is driven in accordance with a control signal from the image sensing controller 24 so that the direction of the patient 50 with respect to the X-ray beam from the X-ray generator 40 can be changed. An X-ray detector 52 for detecting the X-ray beam transmitted through the patient 50 and the imaging bed 48 is placed under the imaging bed 48.

The X-ray detector 52 comprises a stack of a grid 54, scintillator 56, photodetector array 58, and X-ray exposure amount monitor 60, and a driver 62 for driving the photodetector array 58. The grid 54 is arranged to reduce the influence of X-ray scattering caused when the X-rays are transmitted through the patient 50. The grid 54 is formed from an X-ray non-absorbing member and X-ray absorbing member and has a stripe structure of, e.g., Al and Pb. In X-ray irradiation, to prevent moire by the matrix ratio relationship between the photodetector array 58 and the grid 54, the X-ray detector 52 vibrates the grid 54 in accordance with a control signal from the driver 62 on the basis of settings from the image sensing controller 24.

In the scintillator 56, the matrix substance of phosphor is excited (absorbed) by high-energy X-rays, and fluorescent light in the visible region is generated by the recombination energy. That is, the X-rays are converted into visible light.

The fluorescent light is generated by the matrix itself such as $CaWo_4$ or $CdWO_4$ or luminescence center substance such as CsI:Tl or ZnS:Ag doped into the matrix. The photodetector array 58 converts the visible light obtained by the scintillator 56 into an electrical signal.

The X-ray exposure amount monitor 60 is arranged in order to monitor the X-ray transmission amount. The X-ray exposure amount monitor 60 may directly detect X-rays using a silicon crystal light-receiving element or the like, or detect fluorescent light generated by the scintillator 56. In this embodiment, the X-ray exposure amount monitor 60 is formed from an amorphous silicon light-receiving element formed on the lower surface of the substrate of the photodetector array 58, detects visible light (proportional to the X-ray dose) transmitted through the photodetector array 58, and transmits the light amount information to the image sensing controller 24. The image sensing controller 24 controls the X-ray generator 40 on the basis of the information from the X-ray exposure amount monitor 60 to adjust the X-ray dose.

The driver 62 drives the photodetector array 58 under the control of the image sensing controller 24 to read a signal from each pixel. Operations of the photodetector array 58 and driver 62 will be described later in detail.

In the diagnosis room 14, an image processing terminal 70 for processing an image from the LAN board 36 or assisting the diagnosis, a video display monitor 72 for outputting an image (moving image/still image) from the LAN board 36, an image printer 74, and a file server 76 for storing image data are prepared.

A control signal from the system controller 20 to each device can be generated by an instruction from the operator interface 22 in the X-ray control room 12 or the image processing terminal 70 in the diagnosis room 14.

Basic operation of the system controller 20 will be described next.

On the basis of an instruction from the operator 21, the system controller 20 outputs an imaging condition instruction to the image sensing controller 24 for controlling the sequence of the X-ray image sensing system. On the basis of the instruction, the image sensing controller 24 drives the X-ray generator 40, imaging bed 48, and X-ray detector 52 to obtain an X-ray image. The X-ray image signal output from the X-ray detector 52 is supplied to the image processor 26, subjected to image processing designated by the operator 21, displayed on the monitor 30 as an image, and simultaneously, stored in the storage device 28 as basic image data. The system controller 20 also executes image re-processing and display of its result, image data transfer to a device on the network, storage, video display, and film printing on the basis of instructions from the operator 21.

Basic operation of the system shown in FIG. 7 will be described in accordance with the signal flow.

The high-voltage source 44 of the X-ray generator 40 applies a high voltage for generating X-rays to the X-ray tube 42 in accordance with a control signal from the X-ray tube 42. The X-ray tube 42 generates an X-ray beam. The patient 50 as an object to be examined is irradiated with the generated X-ray beam through the X-ray stop 46. The X-ray stop 46 is controlled by the image sensing controller 24 in accordance with the position where the object is to be irradiated with the X-ray beam. That is, the X-ray stop 46 shapes the X-ray beam as the image sensing region changes not to perform unnecessary X-ray irradiation.

The X-ray beam output from the X-ray generator 40 passes through the patient 50 who lies on the imaging bed 48 transparent to X-rays, and the imaging bed 48 and enters the X-ray detector 52. The imaging bed 48 is controlled by the image sensing controller 24 such that the X-ray beam passes through the object to be examined at different portions or in different directions.

The grid 54 of the X-ray detector 52 reduces the influence of X-ray scattering caused by passing the X-ray beam through the patient 50. To prevent moire by the matrix ratio relationship between the photodetector array 58 and the grid 54, the image sensing controller 24 vibrates the grid 54 in X-ray irradiation. In the scintillator 56, the matrix substance of phosphor is excited (absorbs the X-rays) by the high-energy X-rays, and fluorescent light in the visible region is generated by the recombination energy generated at that time. The photodetector array 58 arranged adjacent to the scintillator 56 converts the fluorescent light generated by the scintillator 56 into an electrical signal. That is, the scintillator 56 converts the X-ray image into a visible light image, and the photodetector array 58 converts the visible light image into an electrical signal. The X-ray exposure amount monitor 60 detects the visible light (proportional to the X-ray dose) transmitted through the photodetector array 58 and supplies the detection amount information to the image sensing controller 24. The image sensing controller 24 controls the high-voltage source 44 on the basis of the X-ray exposure amount information to cut off or adjust the X-rays. The driver 62 drives the photodetector array 58 under the control of the image sensing controller 24 to read a pixel signal from each photodetector. Details of the photodetector array 58 and driver 62 will be described later.

The pixel signal output from the X-ray detector 52 is supplied to the image processor 26 in the X-ray control room 12. Since large noise is generated by X-ray generation in the X-ray room 10, the signal transmission path from the X-ray detector 52 to the image processor 26 must be highly resistant to noise. More specifically, a digital transmission system having an advanced error correction function or a shielded twisted pair line or optical fiber by a differential driver is preferably used.

Although details will be described later, the image processor 26 switches the image signal display format on the basis of an instruction from the system controller 20, executes image signal correction, space filtering, and recursive processing in real time, and also can execute grayscale processing, scattered ray correction, and DR compression processing. The image processed by the image processor 26 is displayed on the screen of the monitor 30.

Simultaneously with real-time image processing, image information (basic image) that has undergone only image correction is stored in the storage device 28. The image information stored in the storage device 28 is reconstructed to satisfy a predetermined standard (e.g., Image Save & Carry (IS&C)) and stored in the external storage device 34 and a hard disk in the file server 76 on the basis of an instruction from the operator 21.

The devices in the X-ray control room 12 are connected to a LAN (or WAN) through the LAN board 36.

A plurality of X-ray image sensing systems can be connected to the LAN. The LAN board 36 outputs image data in accordance with a predetermined protocol (e.g., Digital Imaging and Communications in Medicine (DICOM)). By displaying the X-ray image on the screen of the monitor 72 connected to the LAN as a high-resolution still image or moving image, real-time remote diagnosis by a doctor is possible almost simultaneously with X-ray imaging.

Figure 8:
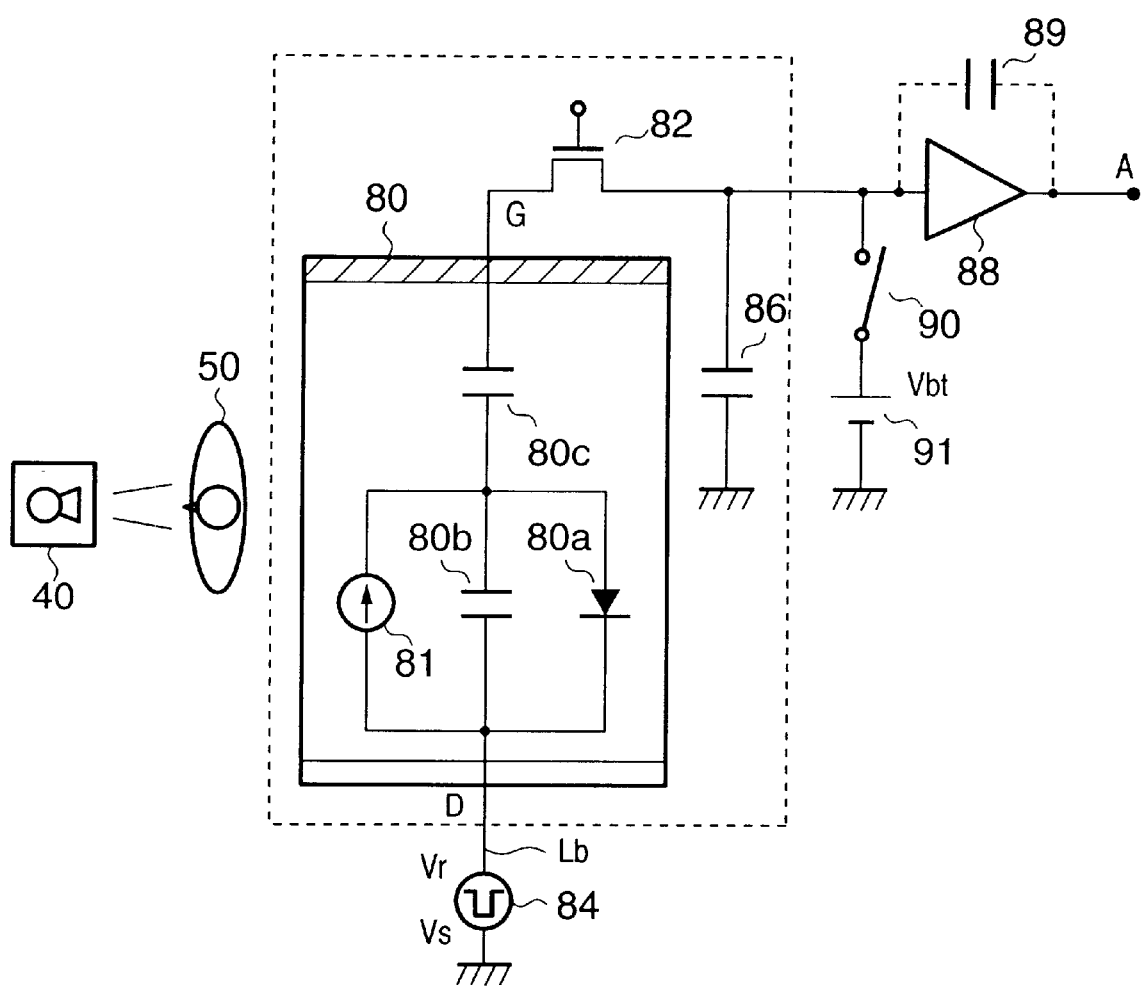
FIG. 8 is a circuit diagram showing an equivalent circuit of a first photodetection section.

FIG. 8 is a circuit diagram showing an equivalent circuit of a construction unit of the photodetector array 58.

One element is formed from a photodetection section 80 and a switching thin film transistor (TFT) 82 for controlling charge accumulation and read and is generally formed from amorphous silicon (a-Si) on a glass substrate. The photodetection section 80 is formed from a parallel circuit of a photodiode 80*a* and capacitor 80*b*, and a capacitor 80*c* connected in series with the capacitor 80*b*. Charges by the photoelectric conversion effect are described as a constant current source 81. The capacitor 80*b* may be either the parasitic capacitance of the photodiode 80*a* or an additional capacitor for improving the dynamic range of the photodiode 80*a*. The common bias electrode (to be referred to as a D electrode hereinafter) of the photodetection section 80 is connected to a bias power supply 84 through a bias line Lb. An electrode (to be referred to as a G electrode hereinafter) on the side of the switching TFT 82 of the photodetection section 80 is connected to a capacitor 86 and charge reading preamplifier 88 through the switching TFT 82. The input to the preamplifier 88 is also connected to ground through a reset switch 90 and signal line bias power supply 91.

Device operation of the photodetection section 80 will be described with reference to FIGS. 9A to 9C.

Figure 9A:
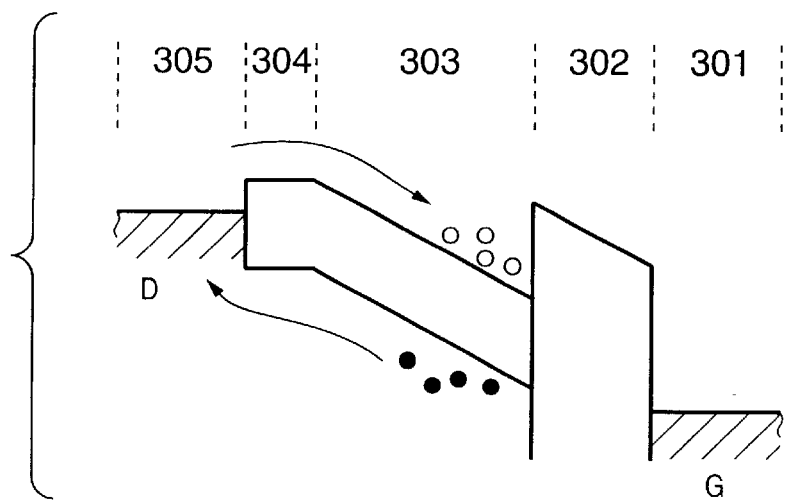
FIGS. 9A to 9C are views showing the energy band of the first photodetection section.
Figure 9B:
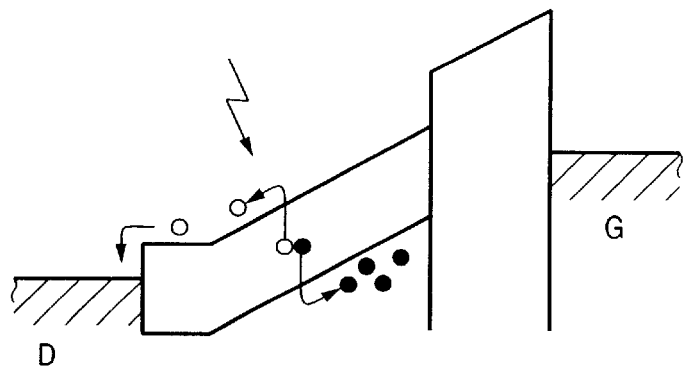
Figure 9C:
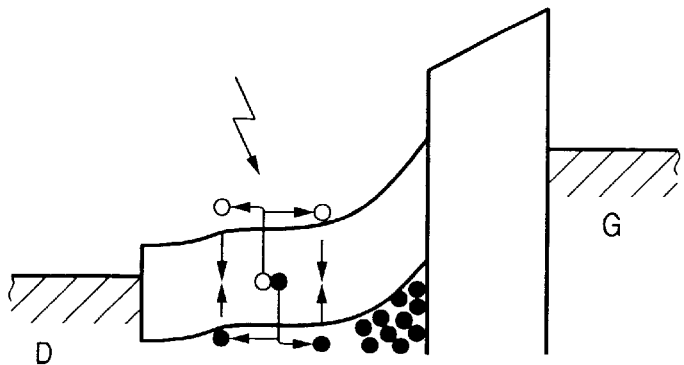

FIGS. 9A and 9B are views showing the energy band of a photoelectric conversion element that exhibits the refresh and photoelectric conversion mode operations of this embodiment. FIGS. 9A and 9B show states in the direction of thickness of each layer. A lower electrode (G electrode) 301 is formed from Cr. An insulating layer 302 is formed from SiN and inhibits both electrons and holes from passing. The thickness of the insulating layer 302 is set to be 50 nm or more such that electrons and holes cannot move by the tunnel effect. A photoelectric conversion semiconductor layer 303 is formed from an intrinsic semiconductor layer of hydrogenated amorphous silicon a-Si. An injection inhibiting 304 is formed from an n-type a-Si layer for inhibiting holes from being injected into the photoelectric conversion semiconductor layer 303. An upper electrode (D layer) 305 is formed from Al. In this embodiment, the D electrode does not completely cover the n-layer. However, since electrons freely move between the D electrode and the n-layer, the D electrode and n-layer always have an equipotential state. The following description will be made assuming this. This photoelectric conversion element performs two types of operation: refresh mode and photoelectric conversion mode in accordance with the manner the voltage is applied to the D and G electrodes.

Referring to FIG. 9A, a potential negative with respect to the G electrode is applied to the D electrode. Holes represented by solid dots in the mode shown in FIG. 9B is held for a certain period, the state returns to the refresh mode shown in FIG. 9A again. The holes that are staying in the i-layer 303 are moved to the D electrode, as described above, and simultaneously, a current corresponding to the holes flows. The number of holes corresponds to the total amount of light incident during the photoelectric conversion mode period. At this time, a current corresponding to the number of electrons injected into the i-layer 303 also flows. The number of electrons is almost constant and is detected by subtraction. That is, the photoelectric conversion element of this embodiment can output the amount of light incident in real time and simultaneously output the total amount of light incident for a given period.

However, when the period of the photoelectric conversion mode becomes long due to some reason, or the illuminance of incident light is high, no current may flow although light is incident. This is because a number of holes stay in the i-layer 303 and are recombined with holes in the i-layer 303, as shown in FIG. 9C. If the light incident state changes in this state, a current may unstably flow. When the mode is returned to the refresh mode, the holes in the i-layer 303 are swept, and a current proportional to light flows again in the next photoelectric conversion mode.

In the above description, in sweeping holes in i-layer 303 are moved to the D electrode by the electric field. Simultaneously, electrons represented by hollow dots are injected into the i-layer 303. At this time, some holes and electrons are recombined in the n-layer 304 and i-layer 303 and disappear. When this state continues for a sufficiently long time, the holes in the i-layer 303 are swept from the i-layer 303.

To change this state to the photoelectric conversion mode shown in FIG. 9B, a potential positive with respect to the G electrode is applied to the D electrode. Electrons in the i-layer 303 are instantaneously moved to the D electrode. However, holes are not moved to the i-layer 303 because the n-layer 304 acts as an injection inhibiting layer. When light becomes incident on the i-layer 303 in this state, the light is absorbed to generate electron-hole pairs. The electrons are moved to the D electrode by the electric field, and the holes move through the i-layer 303 and reach the interface between the i-layer 303 and the insulating layer 302. However, since the holes cannot enter the insulating layer 302 and move to the interface to the insulating layer 302 in the i-layer 303, a current flows from the G electrode to maintain the electrical neutrality. This current corresponds to the electron-hole pairs generated by the light and is therefore proportional to the incident light. After the state in the photoelectric conversion the i-layer 303 in the refresh mode, it is ideal to sweep all holes. However, even when some holes are extracted, an effect can be obtained, and a current equal to that described above can be obtained without any problem. That is, it is only necessary to prevent the state shown in FIG. 9C in the detection opportunity in the next photoelectric conversion mode, and it suffices to determine the potential of the D electrode with respect to the G electrode in the refresh mode, the period of the refresh mode, and the characteristics of the n-layer 304 as an injection inhibiting layer. Electron injection into the i-layer 303 in the refresh mode is not a necessary condition. The potential of the D electrode with respect to the G electrode is not limited to a negative potential. When a number of holes stay in the i-layer 303, the electric field in the i-layer 303 is applied in a direction to move the holes to the D electrode even when the potential of the D electrode is higher than that of the G electrode. For the characteristics of the n-layer 304 as an injection inhibiting layer as well, the capability of injecting electrons into the i-layer 303 is not a necessary condition.

Referring back to FIG. 8, the signal read from one pixel will be described.

First, the switching TFT 82 and reset switch 90 are temporarily turned on to set the bias power supply 84 at a potential in the refresh mode. After the capacitors 80*b* and 80*c* are reset, the bias power supply 84 is set at a potential in the photoelectric conversion mode, and the switching TFT 82 and reset switch 90 are sequentially turned off. After that, X-rays are generated to irradiate the patient 50. The scintillator 56 converts the X-ray image transmitted through the patient 50 into a visible light image. The photodiode 80*a* is turned on by the visible light image to discharge the capacitor 80*b*. The switching TFT 82 is turned on to connect the capacitors 80*b* and 86. Information in the capacitor 80*c* is also transmitted to the capacitor 86. The voltage by charges accumulated in the capacitor 86 is amplified by the preamplifier 88, or the charges are converted into a voltage by a capacitor 89 indicated by the dotted line, and the voltage is externally output.

Figure 10:
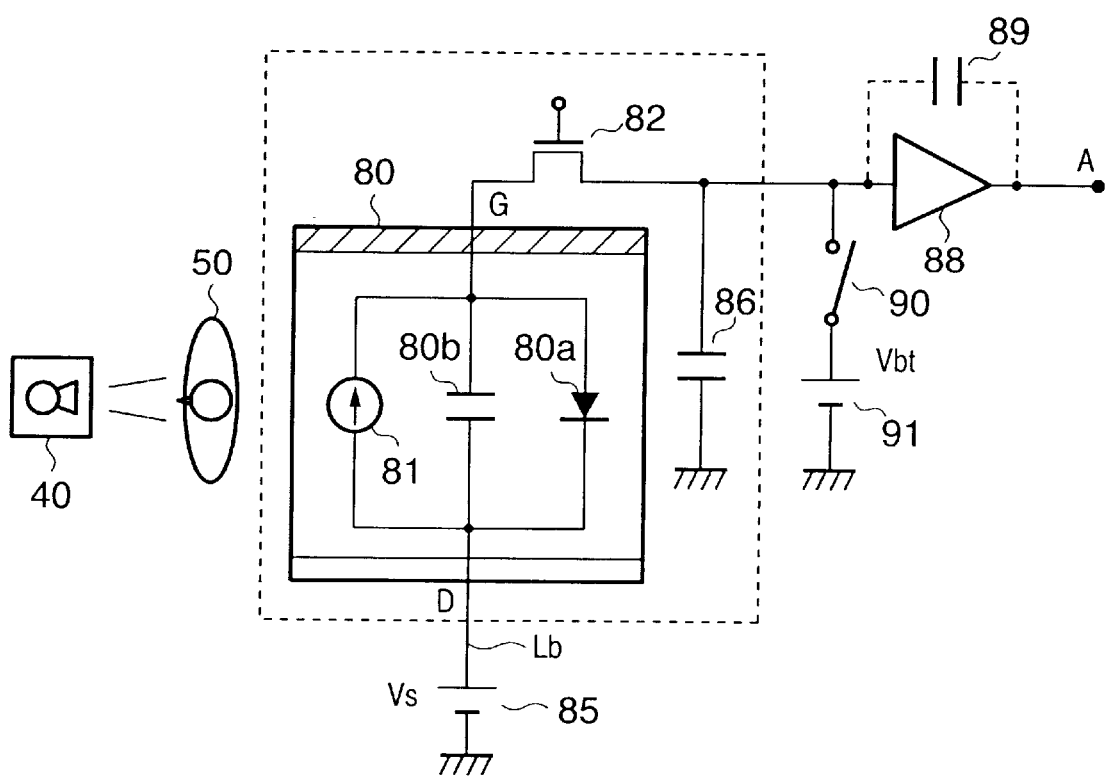
FIG. 10 is a circuit diagram showing an equivalent circuit of a second photodetection section.

FIG. 10 is a circuit diagram showing another equivalent circuit of a construction unit of the photodetector array 58.

One element is formed from the photodetection section 80 and switching thin film transistor (TFT) 82 for controlling charge accumulation and read and is generally formed from amorphous silicon (a-Si) on a glass substrate. The photodetection section 80 is formed from the parallel circuit of the photodiode 80a and capacitor 80b. Charges by the photoelectric conversion effect are described as the constant current source 81. The capacitor 80b may be either the parasitic capacitance of the photodiode 80a or an additional capacitor for improving the dynamic range of the photodiode 80a. The cathode of the photodetection section 80 (photodiode 80a) is connected to a bias power supply 85 through the bias line Lb as a common electrode (D electrode). The anode of the photodetection section 80 (photodiode 80a) is connected from the gate electrode (G electrode) to the capacitor 86 and charge reading preamplifier 88 through the switching TFT 82. The input to the preamplifier 88 is also connected to ground through the reset switch 90 and signal line bias power supply 91.

First, the switching TFT 82 and reset switch 90 are temporarily turned on to reset the capacitor 80b. Then, the switching TFT 82 and reset switch 90 are turned off. After that, X-rays are generated to irradiate the patient 50. The scintillator 56 converts the X-ray image transmitted through the patient 50 into a visible light image. The photodiode 80a is turned on by the visible light image to discharge the capacitor 80b. The switching TFT 82 is turned on to connect the capacitors 80b and 86. Information of the discharge amount of the capacitor 80b is also transmitted to the capacitor 86. The voltage by charges accumulated in the capacitor 86 is amplified by the preamplifier 88, or the charges are converted into a voltage by the capacitor 89 indicated by the dotted line, and the voltage is externally output.

Figure 11:
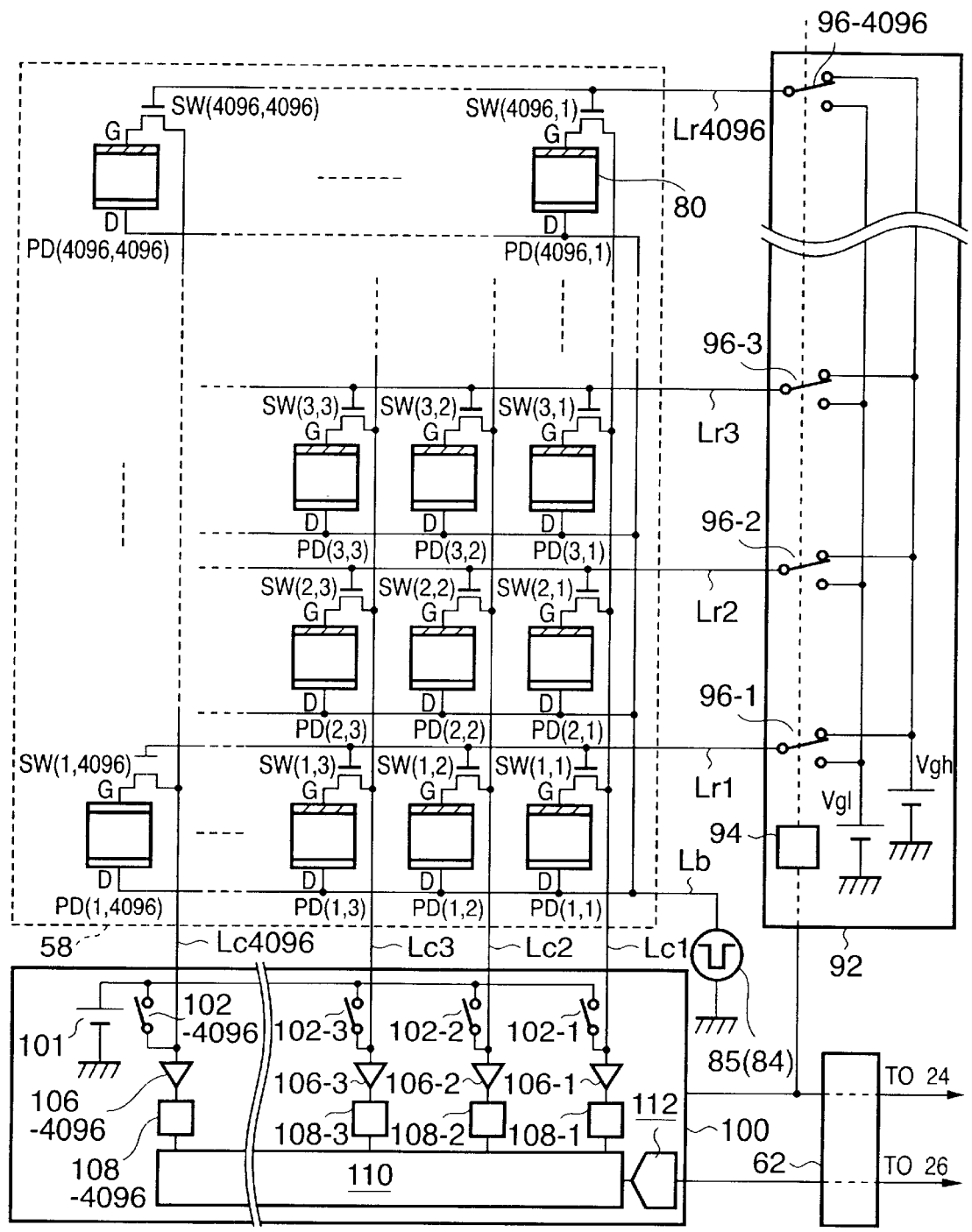
FIG. 11 is a schematic view showing the arrangement of a photodetector array.

Photoelectric conversion operation when the photoelectric conversion element shown in FIGS. 9 or 10 is expanded to a two-dimensional array will be described next. FIG. 11 is a schematic view showing the equivalent circuit of the photodetector array 58 having photoelectric conversion elements arranged in a two-dimensional array.

Two-dimensional read operation is the same as in the above two types of equivalent circuits, and FIG. 11 shows an arrangement using the equivalent circuit shown in FIG. 10.

The photodetector array 58 is formed from about 2,000× 2,000 to 4,000×4,000 pixels, and the array area is about 200 mm×200 mm to 500 mm×500 mm. Referring to FIG. 11, the photodetector array 58 is formed from 4,096×4,096 pixels, and the array area is 430 mm×430 mm. Hence, the size of one pixel is about 105 μm×105 μm. In this case, 4,096 pixels arranged in the horizontal direction form one block, and 4,096 blocks are arranged in the vertical direction to obtain a two-dimensional structure.

Referring to FIG. 11, the photodetector array having 4,096×4,096 pixels is formed from one substrate. However, four photodetector arrays each having 2,048×2,048 pixels may be combined. In this case, although combining the four photodetector arrays is time-consuming, the yield of each photodetector array improves, and the total yield also improves.

As described with reference to FIGS. 8 and 10, one pixel is formed from one photodetection section 80 and switching TFT 82. Each of photoelectric conversion elements PD (1,1) to (4096,4096) corresponds to the photodetection section 80, and each of transfer switches SW (1,1) to (4096,4096) corresponds to the switching TFT 82. The gate electrode (G electrode) of a photoelectric conversion element PD (m,n) is connected to a common column signal line Lcm for that column through a corresponding switch SW (m,n). For example, the photoelectric conversion elements PD (1,1) to (4096,1) of the first column are connected to a first column signal line Lc1. All the common electrodes (D electrodes) of the photoelectric conversion elements PD (m,n) are connected to the bias power supply 85 through the bias line Lb.

Control terminals of the switches SW (m,n) of the same row are connected to a common row selection line Lrn. For example, the switches SW (1,1) to (1,4096) of the first row are connected to a row selection line Lr1 the row selection lines Lr1 to Lr4096 are connected to the image sensing controller 24 through a line selector 92. The line selector 92 is constituted by an address decoder 94 which decodes a control signal from the image sensing controller 24 and determines a specific photoelectric conversion element from which the signal charges are to be read, and 4,096 switch elements 96 turned on/off in accordance with the output from the address decoder 94. With this arrangement, signal charges can be read from the photoelectric conversion element PD (m,n) connected to the switch SW (m,n) connected to the arbitrary line Lrn. As the simplest structure of the line selector 92, it may be constructed by a shift register used in, e.g., a liquid crystal display.

The column signal lines Lc1 to Lc4096 are connected to a signal read circuit 100 controlled by the image sensing controller 24. In the signal read circuit 100, reset switches 102-1 to 102-4096 reset the column signal lines Lc1 to Lc4096 to a reset reference potential 101. Preamplifiers 106-1 to 106-4096 amplify signal potentials from the column signal lines Lc1 to Lc4096. Sample-and-hold (S/H) circuits 108-1 to 108-4096 sample and hold the outputs from the preamplifiers 106-1 to 106-4096. An analog multiplexer 110 multiplexes the outputs from the sample-and-hold circuits 108-1 to 108-4096 on the time axis. An A/D converter 112 converts the analog output from the multiplexer 110 into a digital signal. The output from the A/D converter 112 is supplied to the image processor 26.

In the photodetector array shown in FIG. 11, 4,096×4,096 pixels are divided into 4,096 columns by the column signal lines Lc1 to Lc4096, and signal charges are simultaneously read from 4,096 pixels per row, transferred to the analog multiplexer 110 through the column signal lines Lc1 to Lc4096, preamplifiers 106-1 to 106-4096, and S/H circuits 108-1 to 108-4096, multiplexed on the time axis, and sequentially converted into a digital signal by the A/D converter 112.

Referring to FIG. 9, the signal read circuit 100 has only one A/D converter 112. Actually, A/D conversion is simultaneously executed by four to 32 systems. This is because the image signal read time must be shortened without unnecessarily increasing the analog signal band and A/D conversion rate. The signal charge accumulation time and A/D conversion time have a close relationship. When high-speed A/D conversion is performed, the band of the analog circuit widens, and a desired S/N ratio can hardly be attained. Normally, the image signal read time need be shortened without unnecessarily increasing the A/D conversion speed. To do this, a number of A/D converters are used to A/D-convert the output from the multiplexer 110. However, the larger the number of A/D converters is, the higher the cost becomes. Considering the above points, an appropriate number of A/D converters are used.

Since the X-ray irradiation time is about 10 to 500 msec, the full screen read time or charge accumulation time is appropriately set on the order of 100 msec or relatively short.

For example, to sequentially drive all pixels to read an image, the analog signal band is set to about 50 MHz, and A/D conversion is performed at a sampling rate of, e.g., 10 MHz. In this case, at least four A/D converters are required. In this embodiment, A/D conversion is simultaneously performed by 16 systems. The outputs from the 16 A/D converters are input to 16 corresponding memories (e.g., FIFO) (not shown). By selectively switching the memories, image data corresponding to one continuous scanning line is transferred to the image processor 26.

Figure 12:
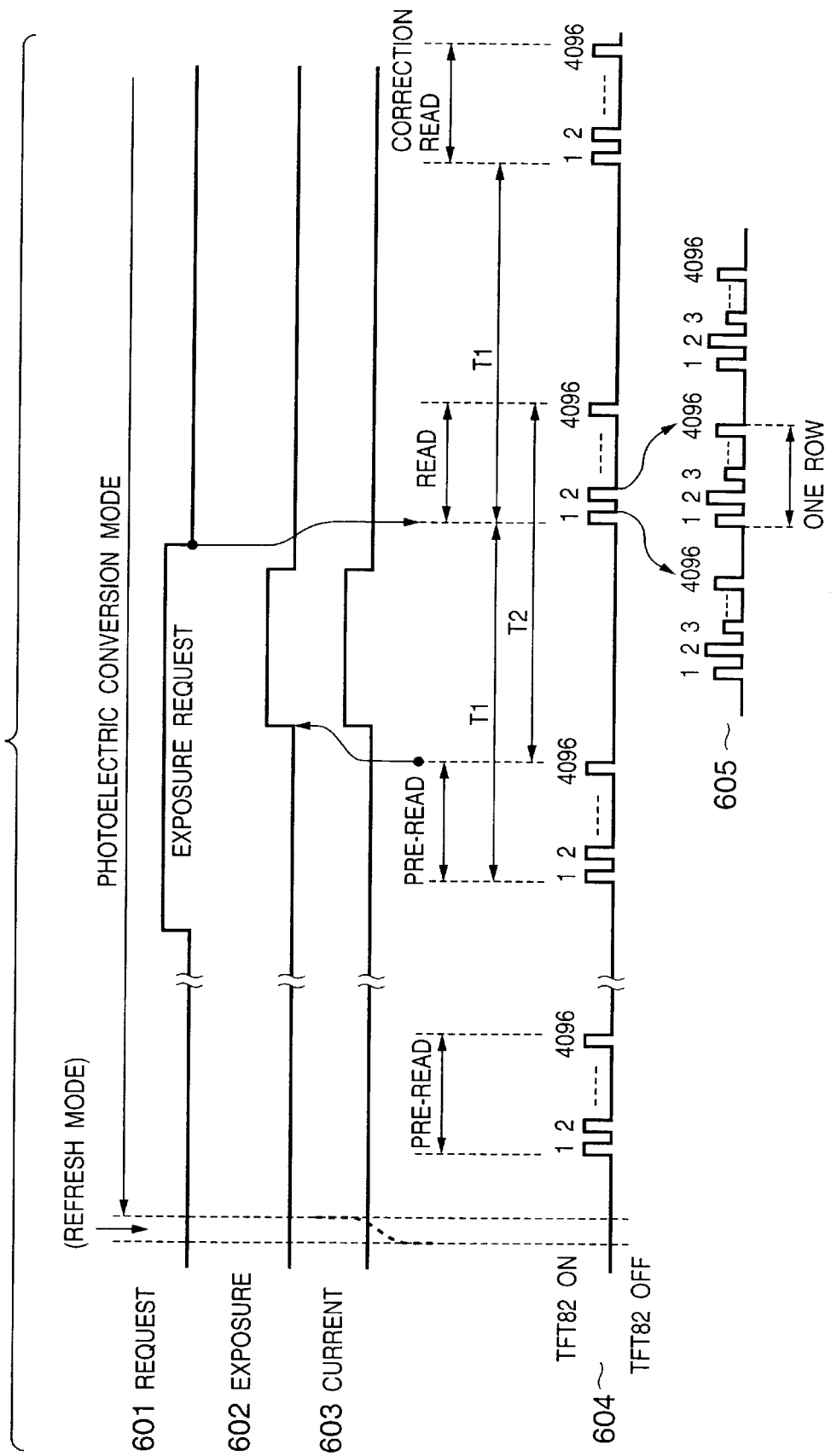
FIG. 12 is a timing chart showing the driving concept of the photodetector array.

FIG. 12 is a schematic timing chart of the sensor read. Two-dimensional drive in sensing a still image by X-ray irradiation of one cycle will be described with reference to FIGS. 11 and 12.

Reference numeral 601 schematically denotes an X-ray exposure request control signal; 602, an X-ray exposure state; 603, a current in the current source 81 in the sensor; 604, a control state of the row selection line Lrn; and 605, an analog input to the A/D converter 112.

In the equivalent circuit sensor shown in FIG. 8, first, the driver 62 sets the bias line to a bias value Vr in the refresh mode, connects all the column signal lines Lc1 to Lc4096 to the reset reference potential 101 to initialize them to a predetermined bias value of the column signal lines Lc, and applies a positive voltage Vgh to all the row selection lines Lr1 to Lr4096. The switches (1,1) to (4096,4096) are turned on to refresh the G electrodes of all the photoelectric conversion elements to Vbt and the D electrodes to Vr.

After that, the driver 62 sets the bias line Lb to a bias value Vs in the photoelectric conversion mode, release all the column signal lines Lc1 to Lc4096 from the reset reference potential 101, and applies a voltage Vg1 to all the row selection lines Lr1 to Lr4096 to turn off the switches (1,1) to (4096,4096). The mode shifts to the photoelectric conversion mode.

Operation from here is common to the equivalent circuit sensors shown in FIGS. 8 and 10, and a description thereof will be commonly done. While keeping the bias line at the bias value Vs in the photoelectric conversion mode, all the column signal lines Lc are connected to the reset reference potential 101 to reset the column signal lines. After that, the positive voltage Vgh is applied to the row selection line Lr1 to turn on the switches (1,1) to (1,4096) and reset the G electrodes of the photoelectric conversion elements of the first column to Vbt. Next, the row selection line Lr1 is set to the positive voltage Vg1 to turn off the switches (1,1) to (1,4096).

All the pixels are reset by sequentially repeating row selection, thereby completing preparation for imaging. Since the above operation is the same as the signal charge read operation except whether signal charges are read, operation after this reset operation is called a "pre-read". During this pre-read operation, all the row selection lines Lr can be simultaneously set to Vgh. In this case, however, when preparation for the read is completed, the signal line potential is largely shifted from the reset voltage Vbt, and a signal with high S/N radio can hardly be obtained. In the above-described example, the row selection lines Lr1 to Lr4096 are reset in this order. However, they can be reset in an arbitrary order under the control of the driver 62 on the basis of the setting of the image sensing controller 24.

An X-ray exposure request is waited while repeating the pre-read operation.

When an exposure request is generated, the pre-read operation is performed again to prepare for image acquisition, and X-ray exposure is waited. When preparation for image acquisition is completed, X-ray exposure is executed in accordance with an instruction from the image sensing controller 24.

After X-ray exposure, signal charges are read from the photoelectric conversion elements 80. First, the voltage Vgh is applied to the row selection line Lr of a certain row (e.g., Lr1) of the photoelectric conversion element array to output accumulated charge signals to the signal lines Lc1 to Lc4096. Signals of 4,096 pixels are simultaneously read from the column signal lines Lc1 to Lc4096 in units of columns.

Next, the voltage Vgh is applied to another row selection line Lr (e.g., Lr2) to output accumulated charge signals to the signal lines Lc1 to Lc4096. Signals of 4,096 pixels are simultaneously read from the column signal lines Lc1 to Lc4096 in units of columns. All pieces of image information are read by sequentially repeating this operation for the 4,096 column signal lines.

During the operation, the charge accumulation time of each sensor corresponds to a time after the reset operation is ended, i.e., the TFT 82 in the pre-read mode is turned off until the TFT 82 is turned on to read charges. Hence, the accumulation time and timing change for each row selection.

After an X-ray image is read, a correction image is acquired. This correction data is necessary to acquire a high-quality image and is used to correct the X-ray image. The basic image acquisition procedure is the same as described above except that no X-ray exposure is performed. The charge accumulation time in reading the X-ray image equals that in reading the correction image.

When high-resolution image information is unnecessary, or the image data read speed need be high, all pieces of image information need not always be read. In accordance with the imaging method selected by the operator 21, the image sensing controller 24 sets a drive instruction of thinning, pixel averaging, or region extraction for the driver 62.

To thin the image data, first, the row selection line Lr1 is selected, and in outputting signals from the column signal lines Lc, signal charges are read from one column while incrementing, e.g., n of Lc2n−1 (n: natural number) one by one from 0. After that, signals are read from one row while incrementing m of Lr2m−1 (m: natural number) one by one from 1. In this example, the number of pixels is thinned to 1/4. The driver 62 thins the number of pixels to 1/9, 1/16, or the like in accordance with a setting instruction from the image sensing controller 24.

For pixel averaging, when the voltage Vgh is simultaneously applied to row selection lines Lr2m and Lr2m+1 during the above-described operation, TFTs 2m and 2n and TFTs 2m+1 and 2n are simultaneously turned on, so that analog addition of two pixels in the column direction can be performed. This means that not only addition of two pixels but also analog addition of a puerility of pixels in the column signal line direction can be easily performed. For addition in the row direction, when adjacent pixels (Lc2n and Lc2n+1) are digitally added after A/D conversion output, the sum of 2×2 square pixels can be obtained together with the above analog addition. Hence, the data can be read at a high speed without wasting the X-ray irradiation.

As another method of decreasing the total number of pixels to increase the read speed, the image read region is limited. To do this, the operator 21 inputs a necessary region from the operator interface 22, the image sensing controller 24 issues an instruction to the driver 62 on the basis of the input region, and the driver 62 changes the data read range and drives the two-dimensional detector array.

In this embodiment, in the high-speed read mode, 1,024×1,024 pixels are read at 30 F/S. That is, in the entire region of the two-dimensional detector array, addition processing of 4×4 pixels is performed to thin the number of pixels to 1/16, and in the smallest range, an image is sensed in a 1,024×1,024 range without thinning. With this image sensing, a digital zoom image can be obtained.

Figure 13:
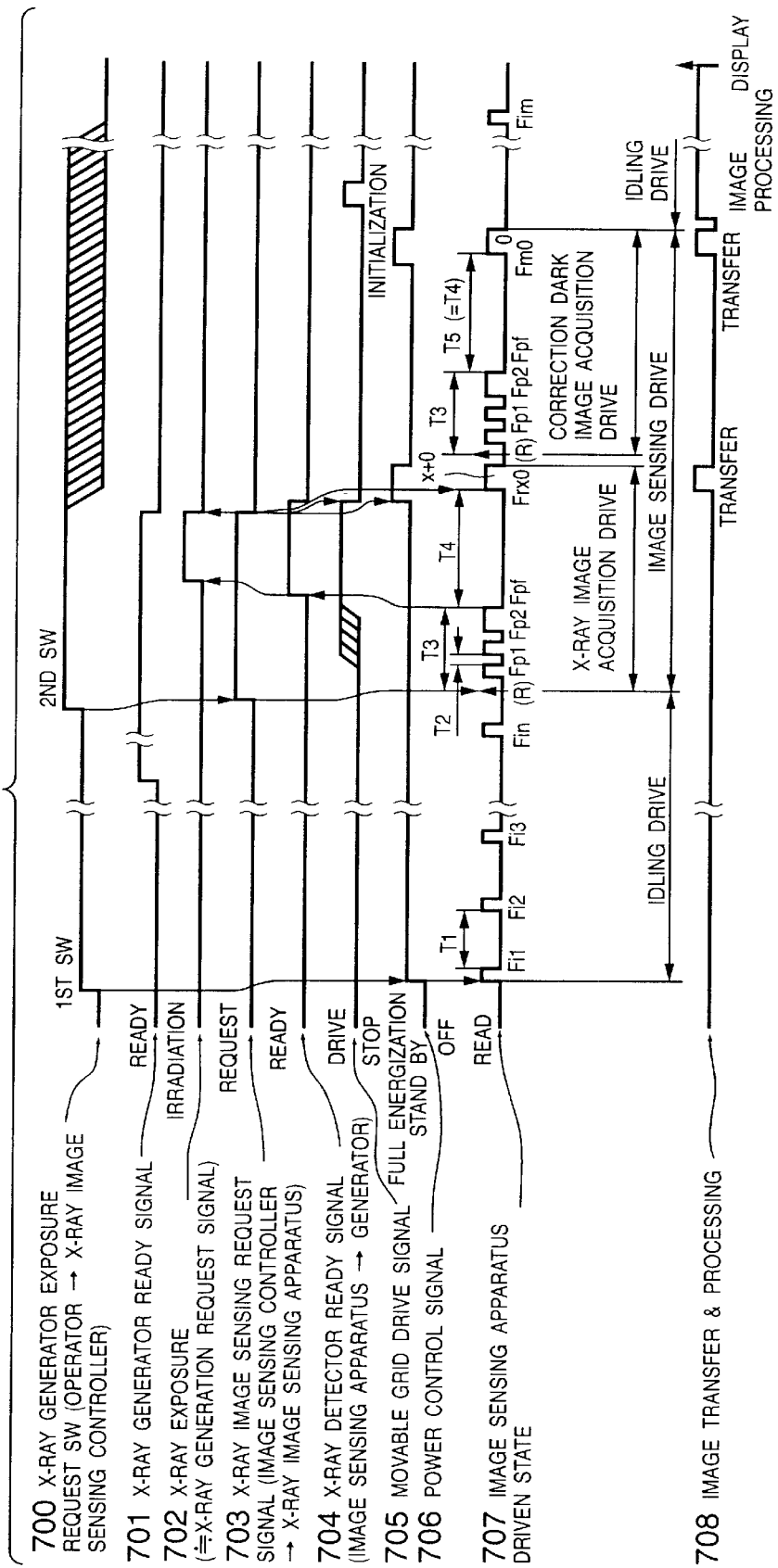
FIG. 13 is a timing chart of an X-ray image sensing system according to the third embodiment.

FIG. 13 is a timing chart including image sensing operation of the X-ray detector 52. The operation of the X-ray detector 52 will be described mainly with reference to FIG. 13.

Reference numeral 701 denotes an image sensing request signal to the operator interface 22; 702, an actual X-ray exposure state; 703, an imaging request signal from the image sensing controller 24 to the driver 62 on the basis of an instruction from the operator 21; 704, an imaging ready signal of the X-ray detector 52; 705, a drive signal for the grid 54; 706, a power control signal in the X-ray detector 52; 707, a driven state of the X-ray detector (especially charge read operation from the photodetector array 58); and 708, an image processing or display state.

Until a detector preparation request or imaging request is input by the operator 21, the driver 62 stands by in a power control off state, as indicated by 706. More specifically, referring to FIG. 11, the row selection lines Lr, column signal lines Lc, and bias line Lb are kept at an equipotential state (especially signal GND level) by a switch (not shown), and no bias is applied to the photodetector array 58. Alternatively, power supply including the signal read circuit 100, line selector 92, and bias power supply 84 or 85 may be cut off to keep the row selection lines Lr, column signal lines Lc, and bias line Lb at the GND potential.

In accordance with an imaging preparation request instruction (701: 1st SW) from the operator 21 to the operator interface 22, the image sensing controller 24 outputs an instruction to shift the X-ray generator 40 to an imaging ready state and shift the X-ray detector 52 to an imaging preparation state. Upon receiving the instruction, the driver 62 applies a bias to the photodetector array 58 and repeats (refresh and) pre-read Fi. The request instruction is, e.g., the 1st SW of the exposure request switch to the X-ray generator (normally, rotor up for the tube or the like is started) or, when a predetermined time (several sec or more) is required by the X-ray detector 52 for imaging preparation, an instruction for starting preparation of the X-ray detector 52.

In this case, the operator 21 need not consciously issue the imaging preparation request instruction to the X-ray detector 52. That is, when patient information or imaging information is input to the operator interface 22, the image sensing controller 24 may interpret it as a detector preparation request instruction and shift the X-ray detector 52 to the detector preparation state.

In the detector preparation state, in the photoelectric conversion mode, to prevent a dark current from being gradually accumulated in the photodetection section 80 after the pre-read and the capacitor 80b (80c) from being held in the saturated state, the (refresh R and) pre-read Fi is repeated at a predetermined interval. This driving performed in the period when no actual X-ray exposure request is generated although the imaging preparation request from the operator 21 has been received, i.e., driving in which the pre-read Fi performed in the detector preparation state is repeated at a predetermined time interval T1 will be referred to as "idling drive" hereinafter. The period when the idling drive is performed in the detector preparation state will be referred to as an "idling drive period" hereinafter. How long the idling drive period continues is undefined in practical use. To minimize the read operation with load on the photodetector array 58 (especially the TFTs 82), the time interval T1 is set to be longer than that in the normal imaging operation, and the pre-read Fi dedicated to idling for which the ON time of the TFTs 82 is shorter than that in a normal read drive Fr. For a sensor that requires the refresh R, the refresh R is performed once for several times of pre-read Fi.

X-ray image acquisition mainly performed by the X-ray detector 52 will be described next.

Drive of the X-ray detector 52 in acquiring an X-ray image is mainly comprised of two image acquisition cycles. As indicated by 707, one is X-ray image acquisition drive, and the other is correction dark image acquisition drive. The drive cycles are almost the same except whether X-ray exposure operation is performed. Each drive cycle has three parts: an image sensing preparation sequence, charge accumulation (exposure window), and image read.

X-ray image acquisition will be described below in accordance with the sequence.

In accordance with an imaging request instruction (701: 2nd SW) from the operator 21 to the operator interface 22, the image sensing controller 24 controls imaging operation while synchronizing the X-ray generator 40 with the X-ray detector 52. In accordance with the imaging request instruction (701: 2nd SW), an imaging request signal is asserted to the X-ray detector at a timing represented by the X-ray exposure request signal 703. The driver performs predetermined image sensing preparation sequence drive as indicated by the imaging driven state 707 in response to the imaging request signal. More specifically, if the refresh is necessary, the refresh is performed. Then, a pre-read FR dedicated to the imaging sequence is performed a predetermined number of times, and a pre-read Fpf dedicated to the charge accumulation state is performed to shift the state to the charge accumulation state (image sensing window: T4).

The number of times and time interval T2 of the pre-read Fp for the image sequence are based on values preset prior to the imaging request from the image sensing controller 24. Optimum drive is automatically selected depending on the image sensing portion or whether the request from the operator 21 represents priority on the operability or image quality. A period (T3) from the exposure request to the end of imaging preparation is required to be short in practical use. Hence, the pre-read Fp dedicated to the image sensing preparation sequence is performed. In addition, independently of the state of idling drive, when an exposure request is generated, the image sensing preparation sequence drive is immediately started to shorten the period (T3) from the exposure request to the end of imaging preparation, thereby improving the operability.

In synchronism with the image sensing preparation of the photodetector array 58, the driver 62 starts moving the grid 54 to sense an image while setting the grid in an optimum moving state in synchronism with the actual X-ray exposure 702. In this case as well, the driver 62 operates on the basis of an optimum grid moving start timing and optimum grid moving speed that are set by the image sensing controller.

In this embodiment, to eliminate the influence of vibration by the operation of the grid 54, the start of movement of the grid 54 is controlled such that a change in acceleration becomes small. In addition, in executing the pre-read Fpf dedicated to the charge accumulation state, which is readily affected by vibration, the grid 54 is controlled to exhibit uniform motion (still state or motion at uniform speed).

When image sensing preparation of the X-ray detector 52 is ended, the driver 62 returns the X-ray detector ready signal 704 to the image sensing controller 24. On the basis of this signal transition, the image sensing controller 24 asserts the X-ray generation request signal 702 to the X-ray generator 40. The X-ray generator 40 generates X-rays while receiving the X-ray generation request signal 702. When a predetermined amount of X-rays is generated, the image sensing controller 24 negates the X-ray generation request signal 702, thereby notifying the X-ray detector 52 of the image acquisition timing. On the basis of this timing, the driver 62 immediately stops the grid 54 and starts operating the signal read circuit 100 that has been in the standby state. After the OFF time of the grid 54 and a predetermined wait time to stabilize the signal read circuit 100, when operation of reading image data from the photodetector array 58 and acquiring a raw image for the image processor 26 on the basis of the driver 62 is ended, the driver 62 shifts the signal read circuit 100 to the standby state again.

In this embodiment, to eliminate the influence of vibration by the operation of the grid 54, the grid 54 is controlled to exhibit uniform motion (including the still state) before drive of an X-ray image acquisition frame Frxo that is most readily affected by vibration noise. Alternatively, a vibration sensor for measuring vibration may be attached to the X-ray detector 52, and the drive of the X-ray image acquisition frame Frxo may be started after confirming that the vibration by the grid or other factors has converged to a predetermined or less value.

Subsequently, the X-ray detector 52 acquires a correction image. That is, the above imaging sequence for imaging is repeated to acquire a dark image without X-ray irradiation, and the correction dark image is transferred to the image processor 26.

In the image sensing sequence, the X-ray exposure time or the like may slightly change between imaging cycles. However, when the same image sensing sequence is reproduced, including such differences, to acquire a rough image, an image with a higher quality can be obtained. However, the operation of the grid 54 is not limited to this. The grid 54 may be set still to suppress the influence of vibration in acquiring the rough image. In this case, after the image is almost acquired, the grid 54 is initialized at a predetermined timing that does not affect the image quality.

Figure 14:
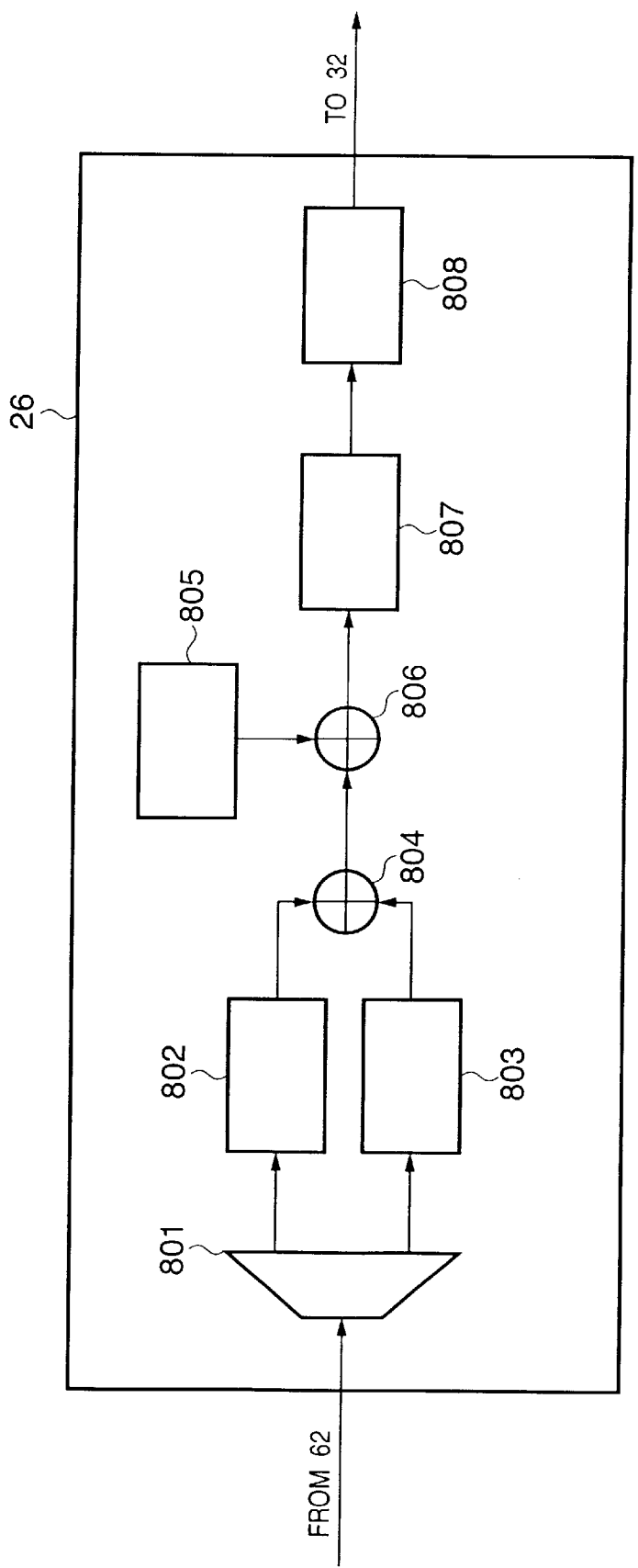
FIG. 14 is a flow block diagram showing processing for an acquired image.

FIG. 14 is a block diagram showing the flow of image data in the image processor 26. Reference numeral 801 denotes a multiplexer for selecting a data path; 802 and 803, X-ray image and rough image frame memories; 804, an offset correction circuit; 805, a gain correction data frame memory; 806, a gain correction circuit; 807, a defect correction circuit; and 808, other image procession circuits.

An X-ray image acquired by the X-ray image acquisition frame Frxo in FIG. 13 is stored in the X-ray image frame memory 802 through the multiplexer 801. A correction image acquired in a correction image acquisition frame Frno is stored in the dark image frame memory 803 through the multiplexer 801.

When the images are almost stored, offset correction (e.g., Frxo−Frno) is performed by the offset correction circuit 804. Subsequently, the gain correction circuit 806 performs gain correction (e.g., (Frxo−Frno)/Fg) using gain correction data Fg which is acquired and stored in the gain correction frame memory in advance. For the data transferred to the defect correction circuit 807, the image is continuously interpolated not to generate any sense of incompatibility at a dead pixel or connections between a plurality of panels of the X-ray detector 52, thus completing sensor-dependent correction processing resulted from the X-ray detector 52. In addition, the image procession circuits 808 execute general image processing such as grayscale processing, frequency processing, and emphasis processing. After that, the processed data is transferred to the display controller 32, and the image is displayed on the monitor 30.

Figure 15:
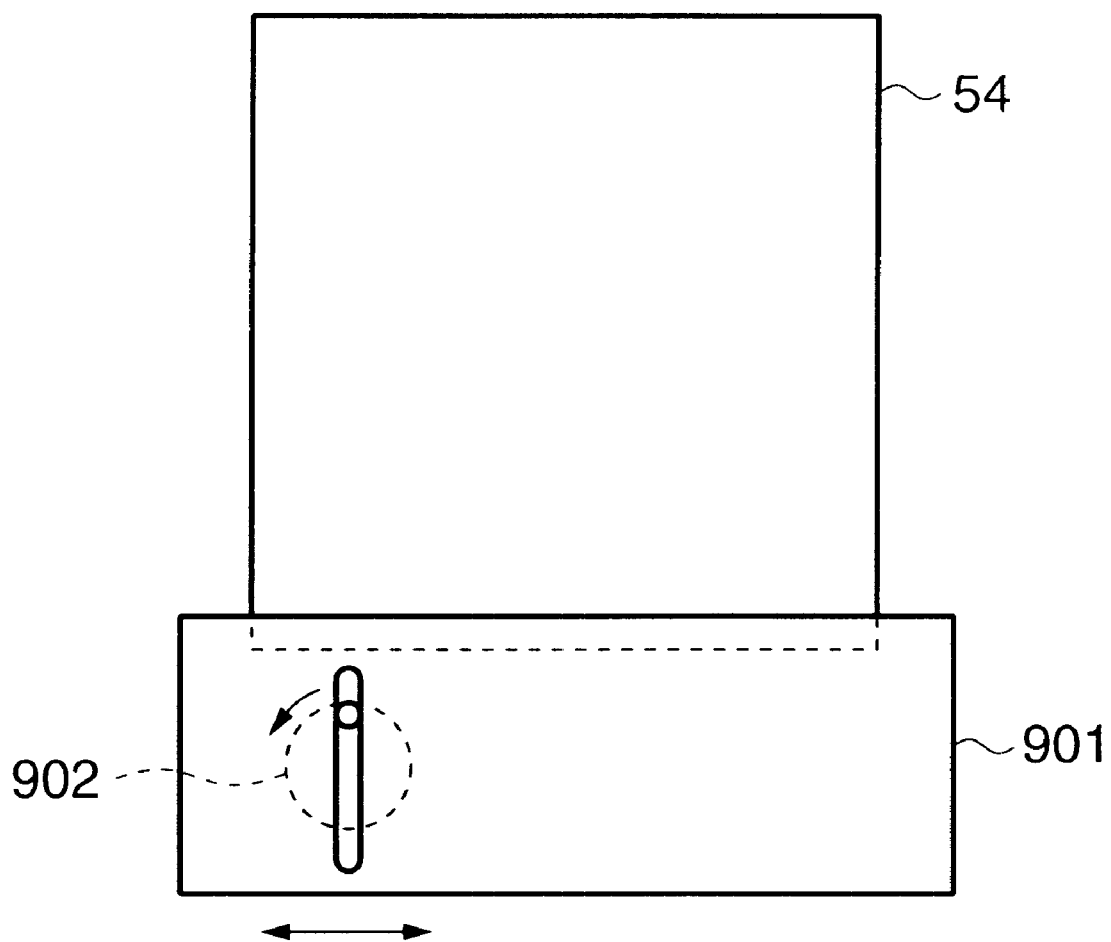
FIG. 15 is a schematic view showing the structure of a first movable grid.
Figure 16:
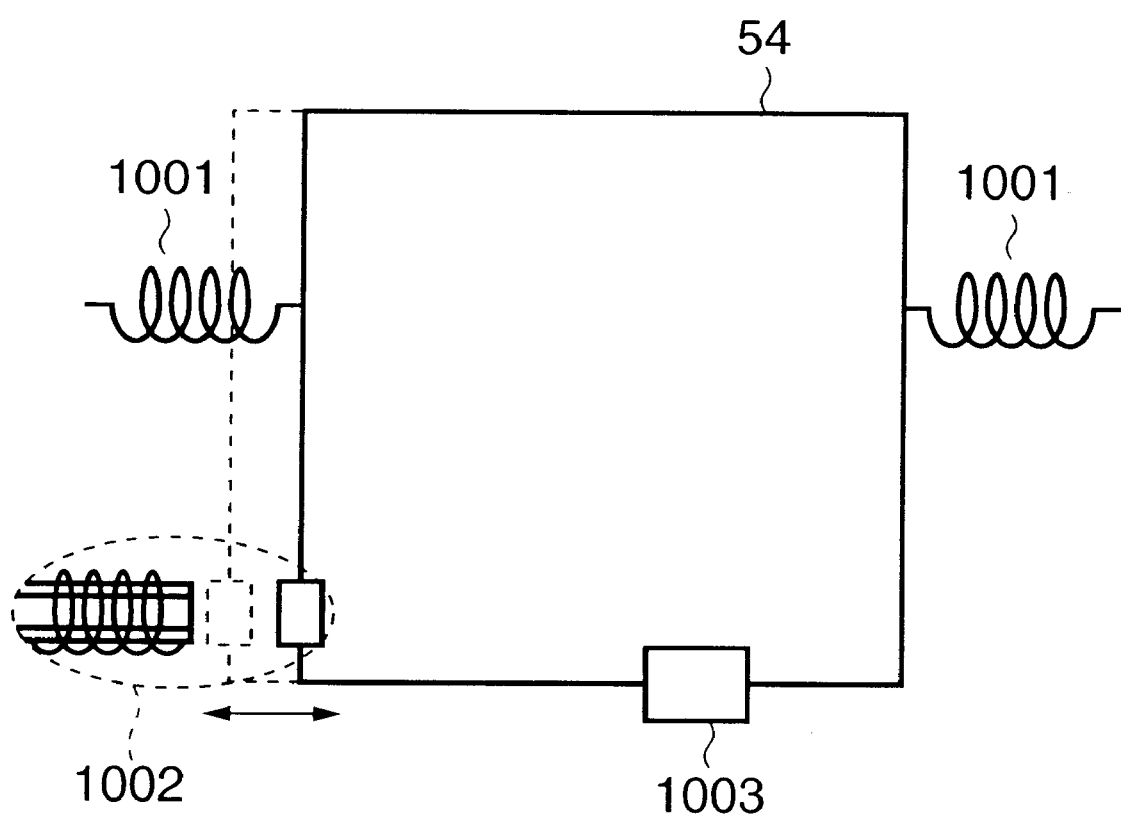
FIG. 16 is a schematic view showing the structure of a second movable grid.

FIGS. 15 and 16 are views showing examples of the driving mechanism of the grid 54.

A frame 901 holds the grid 54. A cam mechanism 902 for vibrating the frame 901 is connected to a rotating mechanism such as a grid driving motor (not shown).

The grid driving motor (not shown) rotates and stops at the grid moving timing shown in FIG. 13 in accordance with an instruction from the driver 62, thereby moving the grid 54 in the direction indicated by the arrow or stopping the grid 54. An elastic member 1001 for moving the grid is formed from, e.g., a spring. A mechanism 1002 for moving the grid 54 to the home position is formed from, e.g., a solenoid. A braking mechanism 1003 stops the grid 54. In the initialization operation, the solenoid mechanism 1002 is operated to move the grid to the home position indicated by the broken line, and the grid is stopped by the braking mechanism 1003. The grid 54 is moved by canceling the braking on the basis of an instruction from the driver 62. The braking mechanism 1003 stops the grid in accordance with an instruction from the driver 62 at a predetermined timing.

As described above, according to the X-ray image sensing apparatus of this embodiment, a satisfactory image can be easily and reliably obtained without any influence of vibration of the grid 54 or the like by a very simple arrangement.

(Fourth Embodiment)

In this embodiment, the internal arrangement of an X-ray room 10 is almost the same as in FIG. 7, and a description of common units will be omitted.

Figure 17:
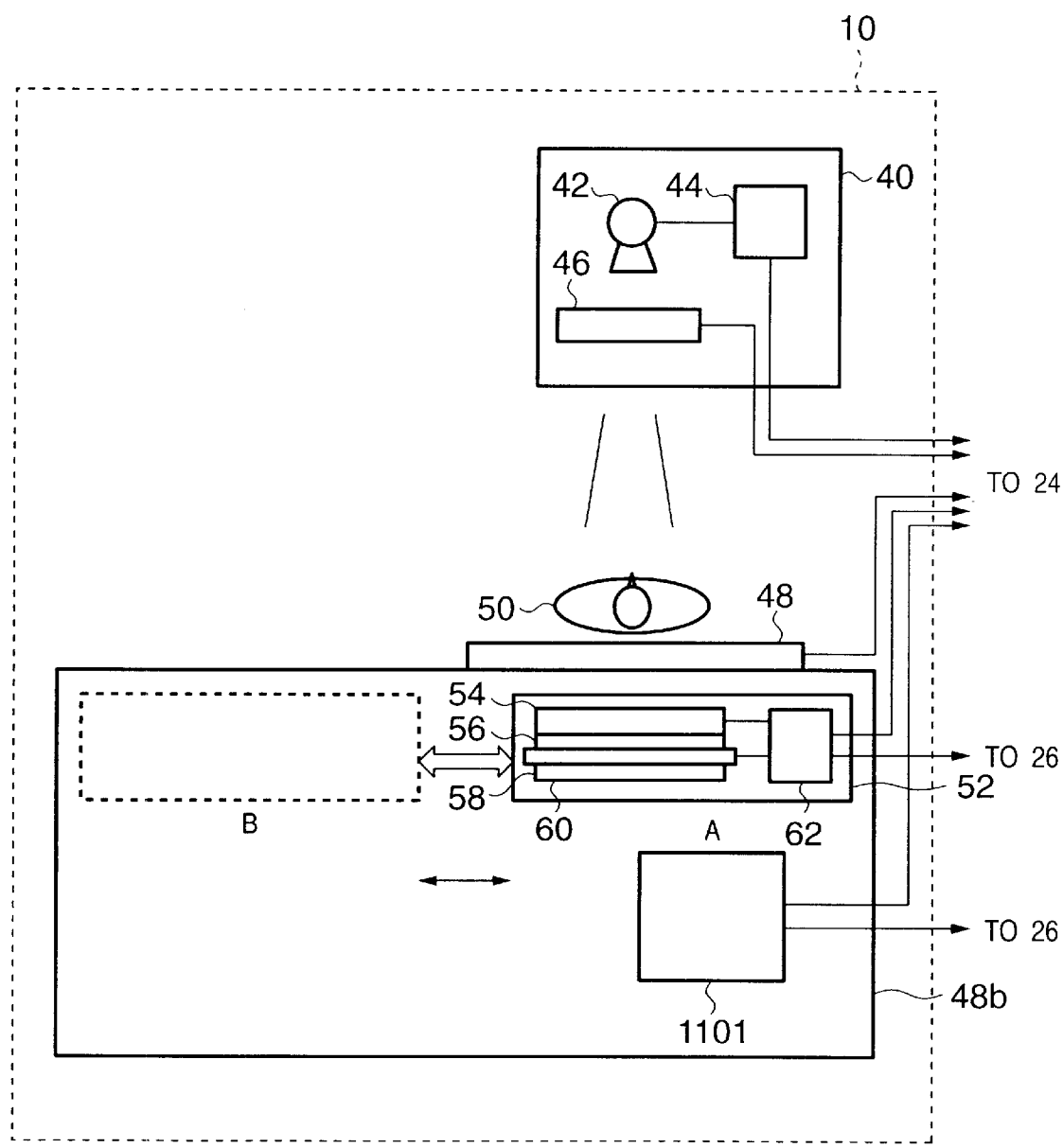
FIG. 17 is a view showing the schematic arrangement of an X-ray image sensing system according to the fourth embodiment.

Reference numeral 48b denotes part of an imaging bed 48 and represents a bed for a fluoroscopic system in FIG. 17. A fluoroscopic II (Image Intensifier) 1101 is controlled by an image sensing controller 24 to transfer an acquired image to an image processor 26 and then display the image on a monitor 30 or monitor dedicated to a fluoroscopic image, like an X-ray detector 52. The X-ray detector 52 is mainly located at a position B during a fluoroscopic image acquisition period and mainly moves to a position A during a simple image acquisition period. The X-ray detector 52 is moved in accordance with an instruction from the image sensing controller 24 to the imaging bed 48. The moving operation is performed by a mechanical means (not shown) for moving the X-ray detector 52.

Figure 18:
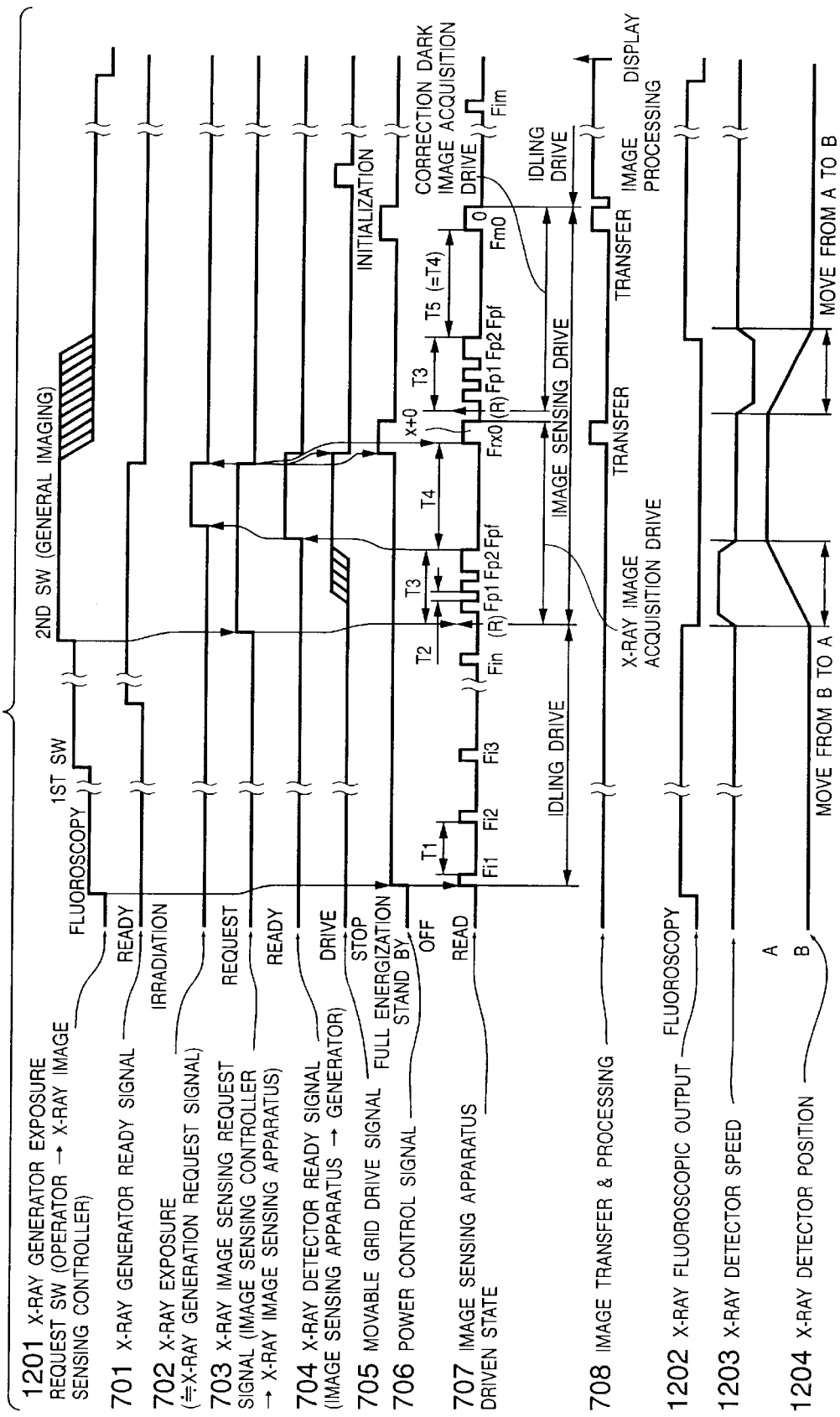
FIG. 18 is a timing chart of an X-ray image sensing system according to the fourth embodiment.

FIG. 18 is a timing chart including image sensing operation of the X-ray detector 52. The operation of the X-ray detector 52 of this embodiment will be described mainly with reference to FIG. 18.

FIG. 18 is almost the same as FIG. 13, and different points will be mainly explained.

Reference numeral 1201 denotes an image sensing request signal to an operator interface 22, which represents a simple X-ray imaging request state in FIG. 13 but a fluoroscopic/simple imaging request in this embodiment. Reference numeral 702 denotes an actual X-ray exposure state; 703, an imaging request signal from the image sensing controller 24 to a driver 62 on the basis of an instruction from an operator 21; 704, an imaging ready signal of the X-ray detector 52; 705, a drive signal for a grid 54; 706, a power control signal in the X-ray detector 52; 707, a driven state of the X-ray detector (especially charge read operation from a photodetector array 58); and 708, an image data transfer state or an image processing or display state. In addition, reference numeral 1202 denotes an X-ray output state for X-ray fluoroscopy; 1203, a concept of moving speed of the X-ray detector 52; and 1204, a position of the X-ray detector 52.

While no request is received from the operator 21, the X-ray detector 52 stands by at the position B of the imaging bed 48.

When a fluoroscopy request 1201 from the operator 21 is detected, fluoroscopic imaging is started (1202), and simultaneously, the X-ray detector 52 starts idling drive (707). When the operator 21 determines the object to be sensed and outputs a general imaging preparation request (1st SW: 1201), the X-ray generator 40 starts preparing for X-ray generation for general imaging and ends the preparation after a predetermined time. When the operator 21 inputs a general imaging request (2nd SW: 1201), the image sensing controller 24 starts X-ray image acquisition drive, instructs the X-ray detector 52 to prepare for imaging (703), stops fluoroscopic imaging (1202), and starts moving the X-ray detector 52 (1203 and 1204).

In this embodiment, the image sensing controller 24 as a control means performs control such that the driver 62 operates the photodetector array 58 in a steady state with a converged vibration, i.e., at a predetermined speed (uniform speed) without acceleration during an operation period related to the read of the X-ray detector 52 as a detection means.

At the start of moving, moving is started while continuously changing the acceleration not to increase the vibration. Since a time T3 until the end of imaging preparation of the X-ray detector 52 is known in advance, the X-ray detector 52 is completely moved to the general imaging position A within a time according to the time T3. However, in the driven state 707, when vibration occurs at the time of a frame Fpf immediately before the end of imaging preparation, noise is readily superposed on the image. To prevent this, immediately after the end of the frame Fpf, stop operation of the X-ray detector 52 is started, and until this time, the X-ray detector 52 is controlled to move at a constant speed without generating any acceleration.

When preparation is ended, the X-ray exposure 702 is performed. Immediately after exposure is ended, an X-ray image acquisition frame Frxo is driven to acquire an X-ray image (707). After the end of X-ray exposure 702, fluoroscopic imaging should be started as soon as possible. After the drive of the X-ray image acquisition frame Frxo is ended, correction dark image acquisition drive is started, and simultaneously, movement of the X-ray detector 52 from the position A to the position B is immediately started (1204). As in the preceding X-ray image acquisition drive, movement is started while continuously changing the acceleration not to increase the vibration. Since the time T3 until the end of imaging preparation of the X-ray detector 52 is known in advance, as in the X-ray image acquisition drive, the X-ray detector 52 is completely moved to the general imaging position B within a time according to the time T3. Contents related to the frame Fpf immediately before the end of imaging preparation are also the same as in the X-ray image acquisition drive. When movement from the position A to the position B is ended, fluoroscopic imaging is resumed, and the fluoroscopic image can be redisplayed from this time. After that, a rough image acquisition frame Frno is driven at a predetermined timing to acquire a rough image. The general image is subjected to predetermined image processing and then displayed on the monitor 30.

For the control, as in the third embodiment, a sensor (not shown) capable of detecting a vibration amount may be arranged in or near the X-ray detector 52, and a predetermined read (e.g., the X-ray image acquisition frame Frxo, dark image acquisition frame Frno, or frame Fpf immediately before the end of imaging preparation) may be started when the vibration becomes equal to or smaller than a predetermined value.

For the control, except a predicted period of vibration in the driver 62, an operation period related to the image read of the X-ray detector 52 may be set, and drive related to image acquisition may be performed during this operation period.

As described above, according to the X-ray image sensing apparatus of this embodiment, a satisfactory image can be easily and reliably obtained without any influence of vibration of the X-ray detector 52 or the like by a very simple arrangement.

(Fifth Embodiment)

In this embodiment, the internal arrangement of an X-ray room 10 is almost the same as in FIG. 7, and a description of common units will be omitted.

Reference numeral 48b denotes part of an imaging bed 48 and represents a bed for a fluoroscopic system in FIG. 17. A fluoroscopic II (Image Intensifier) 1101 is controlled by an image sensing controller 24 to transfer an acquired image to an image processor 26 and then display the image on a monitor 30 or monitor dedicated to a fluoroscopic image, like an X-ray detector 52. The X-ray detector 52 is mainly located at a position B during a fluoroscopic image acquisition period and mainly moves to a position A during a simple image acquisition period. The X-ray detector 52 is moved in accordance with an instruction from the image sensing controller 24 to the imaging bed 48. The moving operation is performed by a mechanical means (not shown) for moving the X-ray detector 52.

Figure 19:
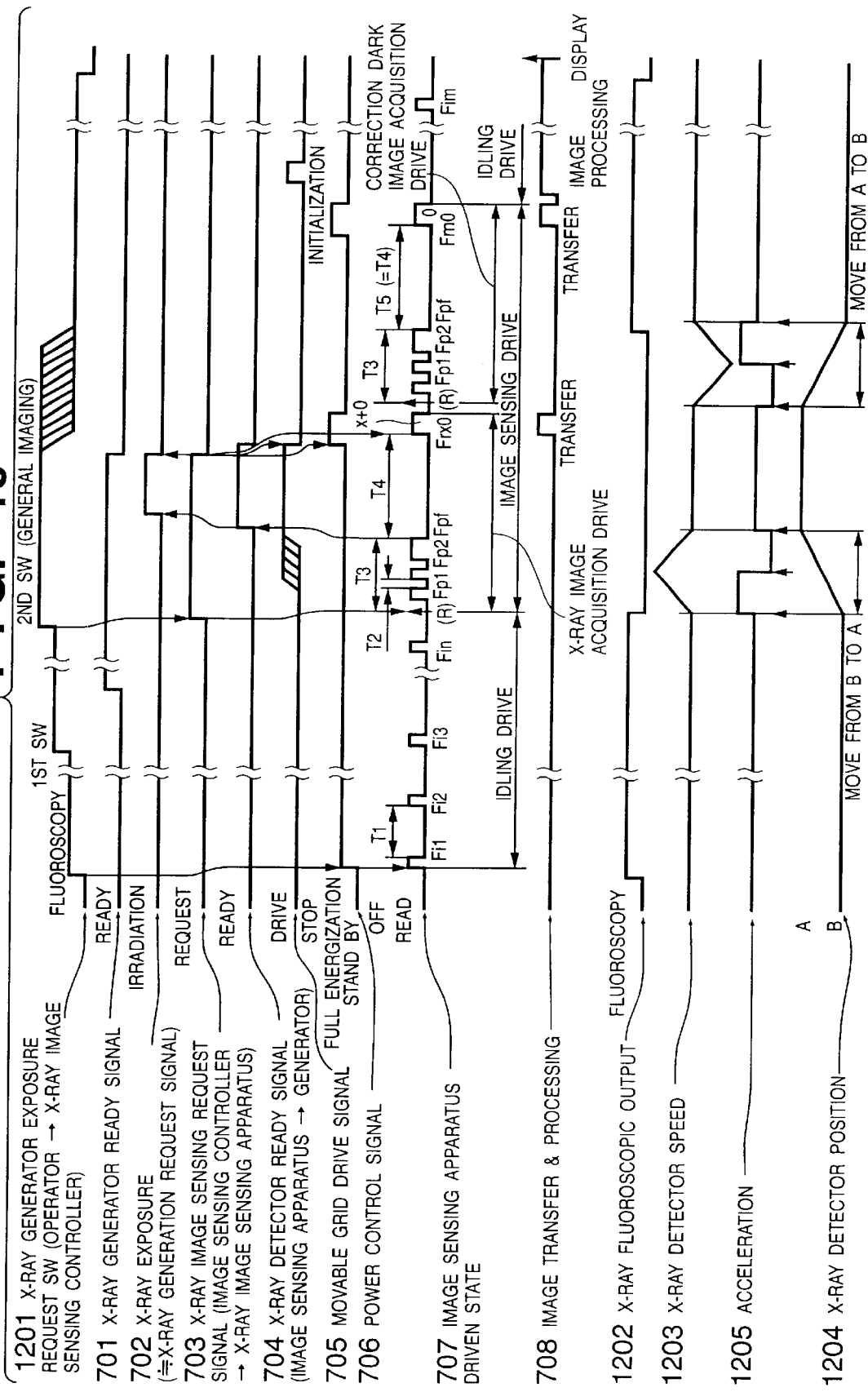
FIG. 19 is a timing chart of an X-ray image sensing system according to the fifth embodiment.

FIG. 19 is a timing chart including image sensing operation of the X-ray detector 52. The operation of the X-ray detector 52 of this embodiment will be described mainly with reference to FIG. 19.

FIG. 19 is almost the same as FIG. 13, and different points will be mainly explained.

Reference numeral 1201 denotes an image sensing request signal to an operator interface 22, which represents a simple X-ray imaging request state in FIG. 13 but a fluoroscopic/simple imaging request in this embodiment. Reference numeral 702 denotes an actual X-ray exposure state; 703, an imaging request signal from the image sensing controller 24 to a driver 62 on the basis of an instruction from an operator 21; 704, an imaging ready signal of the X-ray detector 52; 705, a drive signal for a grid 54; 706, a power control signal in the X-ray detector 52; 707, a driven state of the X-ray detector (especially charge read operation from a photodetector array 58); and 708, an image data transfer state or an image processing or display state. In addition, reference numeral 1202 denotes an X-ray output state for X-ray fluoroscopy; 1203, a concept of moving speed of the X-ray detector 52; and 1204, a position of the X-ray detector 52.

While no request is received from the operator 21, the X-ray detector 52 stands by at the position B of the imaging bed 48.

When a fluoroscopy request 1201 from the operator 21 is detected, fluoroscopic imaging is started (1202), and simultaneously, the X-ray detector 52 starts idling drive (707). When the operator 21 determines the object to be sensed and outputs general imaging preparation request (1st SW: 1201), the X-ray generator 40 starts preparing for X-ray generation for general imaging and ends the preparation after a predetermined time. When the operator 21 inputs a general imaging request (2nd SW: 1201), the image sensing controller 24 starts X-ray image acquisition drive, instructs the X-ray detector 52 to prepare for imaging (703), stops fluoroscopic imaging (1202), and starts moving the X-ray detector 52 (1203 and 1204).

In this embodiment, the image sensing controller 24 as a control means performs control such that the driver 62 operates the photodetector array 58 in a steady state with a converged vibration, i.e., at a predetermined acceleration during an operation period related to the read of the X-ray detector 52 as a detection means.

When a desired acceleration is obtained, the motion preferably shifts to uniformly accelerated motion. In general control, actually, the acceleration abruptly changes (arrows in 1205). Since a time T3 until the end of imaging preparation of the X-ray detector 52 is known in advance, the X-ray detector 52 is completely moved to the general imaging position A within a time according to the time T3. When the movement and frame Fpf are synchronously ended, the time from the 2nd SW to the X-ray exposure 702 can be minimized. Hence, a frame Fpf is required to be ended at the time of predetermined deceleration (negative acceleration). In the driven state 707, when vibration occurs at the time of the frame Fpf immediately before the end of imaging preparation, noise is readily superposed on the image. To prevent this, the frame Fpf is acquired at a timing when the vibration due to the abrupt change in acceleration has converged, and the X-ray detector 52 is stopped immediately after the end of the frame Fpf.

When preparation is ended, the X-ray exposure 702 is performed. After the end of X-ray exposure 702, fluoroscopic imaging should be started as soon as possible. Hence, movement of the X-ray detector 52 from the position A to the position B is started immediately after the end of exposure (1204). Simultaneously, the X-ray image acquisition frame Frxo is driven at the time of uniform acceleration (or uniformly accelerated motion) at the timing when the vibration due to a change in acceleration converges, thereby acquiring an X-ray image. After the end of the X-ray image acquisition frame Frxo, correction dark image acquisition drive is started. Since the time T3 until the end of imaging preparation of the X-ray detector 52 is known in advance, as in the X-ray image acquisition drive, the X-ray detector 52 is completely moved to the general imaging position B within a time according to the time T3. Contents related to the frame Fpf immediately before the end of imaging preparation are also the same as in the X-ray image acquisition drive. When movement from the position A to the position B is ended, fluoroscopic imaging is resumed, and the fluoroscopic image can be redisplayed from this time. After that, a dark image acquisition frame Frno is driven at a predetermined timing to acquire a dark image. The general image is subjected to predetermined image processing and then displayed on the monitor 30.

For the control, as in the third embodiment, a sensor (not shown) capable of detecting a vibration amount may be arranged in or near the X-ray detector 52, and a predetermined read (e.g., the X-ray image acquisition frame Frxo, dark image acquisition frame Frno, or frame Fpf immediately before the end of imaging preparation) may be started when the vibration becomes equal to or smaller than a predetermined value.

For the control, except a predicted period of vibration in the driver 62, an operation period related to the image read of the X-ray detector 52 may be set, and drive related to image acquisition may be performed during this operation period.

As described above, according to the X-ray image sensing apparatus of this embodiment, a satisfactory image can be easily and reliably obtained without any influence of vibration of the X-ray detector 52 or the like by a very simple arrangement.

Three embodiments, the third to fifth embodiments, have been described above. The present invention is applied to a cooling fan or any other potential vibration source.

The present invention also incorporates a case wherein to operate various devices to implement the functions of the above-described embodiments, software program codes for implementing the functions of the embodiments are supplied to a computer in an apparatus or system connected to the devices, and the devices are operated in accordance with a program stored in the computer (or CPU or MPU) of the system or apparatus.

In this case, the software program codes themselves implement the functions of the above-described embodiments, and the program codes themselves and a means for supplying the program codes to the computer, e.g., a storage medium which stores such program codes constitute the present invention. As the storage medium for storing such program codes, for example, a floppy disk, hard disk, optical disk, magnetooptical disk, CD-ROM, magnetic tape, nonvolatile memory card, ROM, or the like can be used.

The functions of the above-described embodiments are implemented when the supplied program codes are executed by the computer. In addition, even when the functions of the above-described embodiments are cooperatively implemented by an operating system (OS) running on the computer or another application software, the program codes are included in the embodiments of the present invention.

The functions of the above-described embodiments are also implemented when the supplied program codes are stored in the memory of a function expansion board inserted into the computer or a function expansion unit connected to the computer, and the CPU of the function expansion board or function expansion unit performs part or all of actual processing on the basis of the instructions of the program codes.

As has been described above, according to the third to fifth embodiments, a radiation image sensing apparatus (image sensing apparatus) and image sensing method which can easily and reliably obtain a satisfactory image without any influence of vibration or a grid or X-ray detection means by a very simple arrangement can be provided.

The present invention is not limited to the above embodiments and various changes and modifications can be made within the spirit and scope of the present invention. Therefore, to apprise the public of the scope of the present invention, the following claims are made.

What is claimed is:

1. An imaging apparatus which has a movable element related to imaging and an image sensing element, and has a function of sensing an image of an object with the image sensing element and reading as an image signal a signal generated by the image sensing element, comprising:

control unit arranged to stop movement of the element related to imaging, and after stopping the movement, starting reading of a signal generated by the image sensing element.

2. The apparatus according to claim 1, wherein the element related to imaging is a grid arranged between the object and the image sensing element.

3. The apparatus according to claim 1, wherein said apparatus further comprises irradiation detection unit arranged to detect irradiation for the object, and said control unit controls the stopping of movement of the element related to imaging on the basis of a detection result from said irradiation detection unit.

4. The apparatus according to claim 1, wherein after stopping movement of a grid, said control unit starts reading the signal from the image sensing element after an elapse of a predetermined time.

5. The apparatus according to claim 4, wherein said control unit determines in advance the predetermined time on the basis of at least one of an irradiation time for the object and a moving speed of the element related to imaging.

6. The apparatus according to claim 1, wherein said apparatus further comprises vibration detection unit arranged to detect a vibration state of the image sensing element due to movement of the element related to imaging, and said control unit controls a start of reading accumulated signal from the image sensing element on the basis of a detection result from said vibration detection unit.

7. The apparatus according to claim 1, wherein irradiation for the object includes radiation irradiation.

8. An imaging apparatus which has a movable element related to imaging and an image sensing element, and has a function of sensing an image of an object with the image sensing element and reading as an image signal a signal generated by the image sensing element, comprising:

drive unit arranged to move the element related to imaging by the image sensing element; and control unit arranged to control said drive unit to operate the element related to imaging at a predetermined speed without any acceleration during an operation period related to reading a signal from the image sensing element.

9. The apparatus according to claim 8, wherein the element related to imaging is a grid inserted between the object and the image sensing element.

10. The apparatus according to claim 8, wherein irradiation for the object includes radiation irradiation.

11. The apparatus according to claim 10, wherein the radiation comprises X-rays.

12. An imaging apparatus which has a movable element related to imaging and an image sensing element, and has a function of sensing an image of an object with the image sensing element and reading as an image signal a signal generated by the image sensing element, comprising:

drive unit arranged to move the element related to imaging; and control unit arranged to control said drive unit to operate the element related to imaging at a uniform acceleration during an operation period related to reading a signal from the image sensing element.

13. The apparatus according to claim 12, wherein the element related to imaging is a grid inserted between the object and the image sensing element.

14. The apparatus according to claim 12, wherein irradiation for the object includes radiation irradiation.

15. The apparatus according to claim 14, wherein the radiation comprises X-rays.

16. An imaging apparatus which has a movable element related to imaging and an image sensing element, and has a function of sensing an image of an object with the image sensing element and reading as an image signal a signal generated by the image sensing element, comprising:

drive unit arranged to move the element related to imaging; and control unit arranged to control execution of a drive operation related to image acquisition upon determining that a value of a vibration is not more than a predetermined value during an operation period related to an image read from the image sensing element.

17. The apparatus according to claim 16, wherein the element related to imaging is a grid inserted between the object and the image sensing element.

18. The apparatus according to claim 16, wherein irradiation for the object includes radiation irradiation.

19. The apparatus according to claim 18, wherein the radiation comprises X-rays.

20. An imaging apparatus having a function of sensing an image of an object with an image sensing element and reading as an image signal a signal generated by the image sensing element, comprising:

drive unit arranged to move the image sensing element; and control unit arranged to stop movement of the image sensing element by said drive unit, and after stopping the movement, starting reading of an accumulated signal from the image sensing element.

21. The apparatus according to claim 20, wherein after stopping movement of the image sensing element, said control unit starts reading the signal from the image sensing element after an elapse of a predetermined time.

22. The apparatus according to claim 20, wherein said apparatus further comprises vibration detection unit arranged to detect a vibration state of the image sensing element, and said control unit controls a start of reading of the signal from the image sensing element on the basis of a detection result from said vibration detection unit.

23. The apparatus according to claim 20, wherein irradiation for the object includes radiation irradiation.

24. An imaging apparatus having a function of sensing an image of an object with an image sensing element and reading as an image signal a signal generated by the image sensing element, comprising:

drive unit arranged to move the image sensing element; and control unit arranged to control said drive unit to operate the image sensing element at a predetermined speed without any acceleration during an operation period related to reading a signal from the image sensing element.

25. The apparatus according to claim 24, wherein irradiation for the object includes radiation irradiation.

26. The apparatus according to claim 25, wherein the radiation comprises X-rays.

27. An imaging apparatus having a function of sensing an image of an object with an image sensing element and reading as an image signal a signal generated by the image sensing element, comprising:

drive unit arranged to move the image sensing element; and control unit arranged to control said drive unit to operate the image sensing element at a uniform acceleration during an operation period related to reading a signal from the image sensing element.

28. The apparatus according to claim 27, wherein irradiation for the object includes radiation irradiation.

29. The apparatus according to claim 28, wherein the radiation comprises X-rays.

30. An imaging apparatus having a function of sensing an image of an object with an image sensing element and reading as an image signal a signal generated by the image sensing element, comprising:

drive unit arranged to move the image sensing element; and control unit arranged to control execution of a drive operation related to image acquisition upon determining that a value of a vibration is not more than a predetermined value during an operation period related to an image read from the image sensing element.

31. The apparatus according to claim 30, wherein irradiation for the object includes radiation irradiation.

32. The apparatus according to claim 31, wherein the radiation comprises X-rays.

33. An imaging method of sensing an image of an object with an image sensing element and reading a signal generated by the image sensing element while moving a movable element related to imaging, comprising:

stopping movement of the element related to imaging, and after stopping the movement, starting reading of a signal from the image sensing element.

34. An imaging method of sensing an image of an object with an image sensing element and reading a signal generated by the image sensing element while moving a movable element related to imaging, comprising:

in moving the element related to imaging at the time of image sensing by the image sensing element, controlling operation of the element related to imaging at a predetermined speed without any acceleration during an operation period related to reading of a signal from the image sensing element.

35. An imaging method of sensing an image of an object with an image sensing element and reading a signal generated by the image sensing element while moving a movable element related to imaging, comprising:

in moving the element related to imaging at the time of image sensing by the image sensing element, controlling operation of the element related to imaging at a uniform acceleration during an operation period related to reading a signal from the image sensing element.

36. An imaging method of sensing an image of an object with an image sensing element and reading a signal generated by the image sensing element while moving a movable element related to imaging, comprising:

in moving the element related to imaging at the time of image sensing by the image sensing element, controlling execution of a drive related to image acquisition upon determining that a value of a vibration of the image sensing element is not more than a predetermined value during an operation period related to an image read from the image sensing element.

37. An imaging method of sensing an image of an object with a movable image sensing element and reading a signal generated by the image sensing element, comprising:

stopping movement of the image sensing element, and after stopping the movement, starting reading of a signal from the image sensing element.

38. An imaging method of sensing an image of an object with a movable image sensing element and reading a signal generated by the image sensing element, comprising:

controlling operation of the image sensing element at a predetermined speed without any acceleration during an operation period related to reading a signal from the image sensing element.

39. An imaging method of sensing an image of an object with a movable image sensing element and reading a signal generated by the image sensing element, comprising:

controlling operation of the image sensing element at a uniform acceleration during an operation period related to reading a signal from the image sensing element.

40. An imaging method of sensing an image of an object with a movable image sensing element and reading a signal generated by the image sensing element, comprising:

controlling execution of a drive operation related to image acquisition upon determining that a value of a vibration of the image sensing element is not more than a predetermined value during an operation period related to an image read from the image sensing element.

41. A computer-readable storage medium wherein said storage medium stores a processing program for executing said imaging method of claim 33.

42. A computer-readable storage medium wherein said storage medium stores a processing program for executing said imaging method of claim 34.

43. A computer-readable storage medium wherein said storage medium stores a processing program for executing said imaging method of claim 35.

44. A computer-readable storage medium wherein said storage medium stores a processing program for executing said imaging method of claim 36.

45. A computer-readable storage medium wherein said storage medium stores a processing program for executing said imaging method of claim 37.

46. A computer-readable storage medium wherein said storage medium stores a processing program for executing said imaging method of claim 38.

47. A computer-readable storage medium wherein said storage medium stores a processing program for executing said imaging method of claim 39.

48. A computer-readable storage medium wherein said storage medium stores a processing program for executing said imaging method of claim 40.

* * * * *